US012744128B2

(12) United States Patent
Eltoukhy et al.

(10) Patent No.: US 12,744,128 B2
(45) Date of Patent: Sep. 22, 2026

(54) PREDICTIVE MODEL FOR DETERMINING CHANGES IN MOLECULAR STATE

(71) Applicant: Guardant Health, Inc., Palo Alto, CA (US)

(72) Inventors: Helmy Eltoukhy, Atherton, CA (US); AmirAli Talasaz, Atherton, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 0 days.

(21) Appl. No.: 19/256,936

(22) Filed: Jul. 1, 2025

(65) Prior Publication Data

US 2025/0329469 A1 Oct. 23, 2025

Related U.S. Application Data

(63) Continuation of application No. 18/642,389, filed on Apr. 22, 2024, now Pat. No. 12,597,524, which is a continuation of application No. 18/173,361, filed on Feb. 23, 2023, now Pat. No. 11,996,202, which is a continuation of application No. 17/814,768, filed on Jul. 25, 2022, now Pat. No. 11,621,083, which is a continuation of application No. 17/690,466, filed on Mar. 9, 2022, now abandoned, which is a continuation of application No. 17/011,835, filed on Sep. 3, 2020, now Pat. No. 11,282,610, which is a continuation of application No. 16/075,105, filed as application No. PCT/US2017/016295 on Feb. 2, 2017, now Pat. No. 11,335,463.

(60) Provisional application No. 62/290,375, filed on Feb. 2, 2016.

(51) Int. Cl.

| | |
|---|---|
| ***G16H 50/30*** | (2018.01) |
| ***C12Q 1/6886*** | (2018.01) |
| ***G16B 20/00*** | (2019.01) |
| ***G16B 20/10*** | (2019.01) |
| ***G16B 20/20*** | (2019.01) |
| ***G16B 40/00*** | (2019.01) |
| ***G16H 50/20*** | (2018.01) |

(52) U.S. Cl.

CPC ........... *G16H 50/30* (2018.01); *C12Q 1/6886* (2013.01); *G16B 20/00* (2019.02); *G16B 20/10* (2019.02); *G16B 20/20* (2019.02); *G16B 40/00* (2019.02); *G16H 50/20* (2018.01); *C12Q 2535/122* (2013.01); *C12Q 2600/156* (2013.01)

(58) Field of Classification Search

CPC ........ G16H 50/30; G16H 50/20; G16B 20/20; G16B 40/00; G16B 20/00; G16B 20/10; C12Q 1/6886

See application file for complete search history.

(56) References Cited

U.S. PATENT DOCUMENTS

| | | | |
|---|---|---|---|
| 9,092,392 | B2 | 7/2015 | Hoff et al. |
| 9,260,753 | B2 | 2/2016 | Xie et al. |
| 9,752,188 | B2 | 9/2017 | Schmitt et al. |
| 2006/0183141 | A1 | 8/2006 | Chang et al. |
| 2009/0247475 | A1 | 10/2009 | Ratain et al. |
| 2009/0319244 | A1 | 12/2009 | West et al. |
| 2010/0184034 | A1 | 7/2010 | Bankaitis-Davis et al. |
| 2010/0255470 | A1 | 10/2010 | Bankaitis-Davis et al. |
| 2010/0279957 | A1 | 11/2010 | Potti et al. |
| 2010/0304989 | A1 | 12/2010 | Hoff et al. |
| 2012/0028264 | A1 | 2/2012 | Shak et al. |
| 2012/0047105 | A1 | 2/2012 | Saigal et al. |
| 2014/0038197 | A1 | 2/2014 | Waldman et al. |
| 2014/0088989 | A1 | 3/2014 | Krishnapuram et al. |
| 2014/0365243 | A1 | 12/2014 | Varadan et al. |
| 2015/0044687 | A1 | 2/2015 | Schmitt et al. |
| 2015/0299810 | A1 | 10/2015 | Kassis |
| 2016/0130649 | A1 | 5/2016 | Xie et al. |
| 2018/0251848 | A1 | 9/2018 | Diehn et al. |
| 2021/0050072 | A1 | 2/2021 | Eltoukhy et al. |

FOREIGN PATENT DOCUMENTS

| | | | |
|---|---|---|---|
| JP | 2003503770 | A | 1/2003 |
| JP | 2009521215 | A | 6/2009 |
| JP | 2010539890 | A | 12/2010 |
| JP | 2011520206 | A | 7/2011 |
| WO | 2009138909 | A1 | 11/2009 |
| WO | 2010028288 | A2 | 3/2010 |
| WO | 2011133477 | A2 | 10/2011 |
| WO | 2012129363 | A2 | 9/2012 |
| WO | 2013142389 | A1 | 9/2013 |
| WO | 2014039556 | A1 | 3/2014 |
| WO | 2014149134 | A2 | 9/2014 |

(Continued)

OTHER PUBLICATIONS

Anonymous: "Gene expression profiling in cancer—Wikipedia", , May 26, 2016 (May 26, 2016), XP055719451, Retrieved from the Internet: URL:https://en.wikipedia.org/w/index.php?title=Gene_expression_profiling_in_cancer&oldid=722257795.

U.S. Appl. No. 16/075,105, Non-Final Office Action mailed Sep. 16, 2021.

U.S. Appl. No. 16/075,105, Response filed Dec. 16, 2021 to Non-Final Office Action mailed Sep. 16, 2021.

U.S. Appl. No. 17/011,835, Non Final Office Action mailed Jan. 29, 2021, 13 pgs.

U.S. Appl. No. 17/011,835, Response filed Nov. 18, 2021 to Non Final Office Action mailed Aug. 19, 2021, 17 pgs.

(Continued)

*Primary Examiner* — Jerry Lin

(74) *Attorney, Agent, or Firm* — Stephen W. Chen

(57) ABSTRACT

A computer-implemented method for training a predictive model to predict a probability that an initial state of a subject will develop a subsequent state. The method includes receiving sequence reads, grouping the sequencing reads into families, constructing a molecular state vector for subjects, storing ordered pairs of vectors, and training the predictive model based on the ordered pairs of vectors. The system supports training the predictive model on a genetic profile of a tumor, a patient profile, and/or treatment profiles.

20 Claims, 10 Drawing Sheets

(56) References Cited

FOREIGN PATENT DOCUMENTS

| | | | |
|---|---|---|---|
| WO | 2014197543 | A1 | 12/2014 |
| WO | 2015183025 | A1 | 12/2015 |
| WO | 2016100638 | A1 | 6/2016 |
| WO | 2016179049 | A1 | 11/2016 |
| WO | 2017062867 | A1 | 4/2017 |

OTHER PUBLICATIONS

U.S. Appl. No. 17/011,835, Final Office Action mailed May 17, 2021, 8 pgs.
U.S. Appl. No. 17/011,835, Non Final Office Action mailed Aug. 19, 2021, 5 pgs.
U.S. Appl. No. 17/011,835, Response filed Apr. 29, 2021 to Non Final Office Action mailed Jan. 29, 2021, 17 pqs.
U.S. Appl. No. 17/011,835, Response filed Jun. 8, 2021 to Final Office Action mailed May 17, 2021, 10 pgs.
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
European Exam Report for EP Application No. 17748191.8 dated Mar. 6, 2023.
Extended European search report and opinion dated Dec. 16, 2019 for EP Application No. 17748191.8.
Geeleher, P. et al. "Clinical drug response can be predicted using baseline gene expression level and in vitro drug sensitivity in cell lines" Genome Biol (2014) 15:R47.
International search report and written opinion dated Apr. 20, 2017 for PCT/US2017/016295.
Japanese Application Serial No. 2018-559686, Notification of Reasons for Refusal mailed Jan. 25, 2021 with English translation, 10 pages.
Japanese Application Serial No. 2018-559686, Office Action mailed Jul. 5, 2021 with English translation, 3 pages.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kinde, et al. Supplemental Information, Detection and quantification of rare mutations with massively parallel sequencing. Proc Natl Acad Sci U S A. Jun. 7, 2011;108(23):1-10.
Kinde, I. et al., "Evaluation of DNA from the Papanicolaou Test to Detect Ovarian and Endometrial Cancers," Sci. Transl. Med. 2013, 5(167):167ra4.
Kinde, I. et al., "FAST-SeqS: a simple and efficient method for the detection of aneuploidy by massively parallel sequencing," PLoS One 2012, 7(7), e41162.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi: 10.1371/journal.pone.0140712.
Lipinski, K. A. et al. "Cancer Evolution and the Limits of Predictability in Precision Cancer Medicine" Trends in Cancer (2016) 2(1):49-63.
Murtaza, M. et al. "Non-invasive analysis of acquired resistance to cancer therapy by sequencing of plasma DNA" Nature (May 2013) 497(7447):108-112.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Office Action for Japanese Patent Application No. 2024-075758, dated May 20, 2025.
Office Action for U.S. Appl. No. 18/173,361 dated Sep. 15, 2023.
Office Action for U.S. Appl. No. 18/642,389, dated Jul. 31, 2024.
Office Action in U.S. Appl. No. 17/814,768, mailed Sep. 15, 2022.
Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Ponomaryova, A.A. et al. "Potentialities of aberrantly methylated circulating DNA for diagnostics and post-treatment follow-up of lung cancer patients" Lung Cancer (2013) 81:397-403.
Schmitt et al. Supplemental Information http://www.pnas.org/content/suppl/2012/08/01/1208715109.DCSupplemental (2012).
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Singapore Application No. 11201806609T Written Opinion dated Nov. 22, 2021 and Invitation to Respond dated Nov. 23, 2021.
Tseng, J-S et al. "Dynamic Plasma EGFR Mutation Status as a Predictor of EGFR-TKI Efficacy in Patients with EGFR-Mutant Lung Adenocarcinoma" J Thoracic Onc (2015) 10(4):603-610.

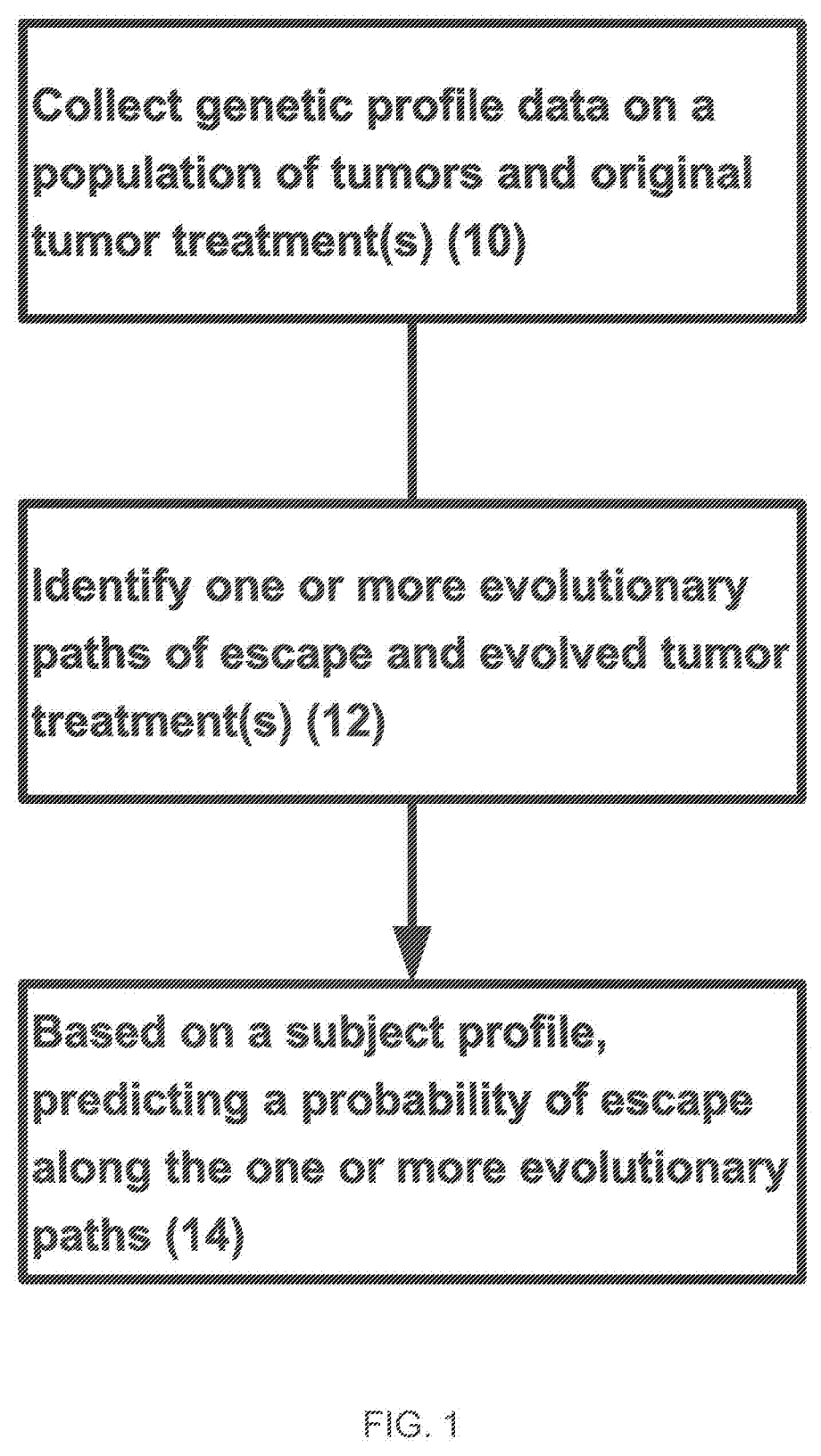

Collect genetic profile data on a population of tumors and original tumor treatment(s) (10)

Identify one or more evolutionary paths of escape and evolved tumor treatment(s) (12)

Based on a subject profile, predicting a probability of escape along the one or more evolutionary paths (14)

FIG. 1

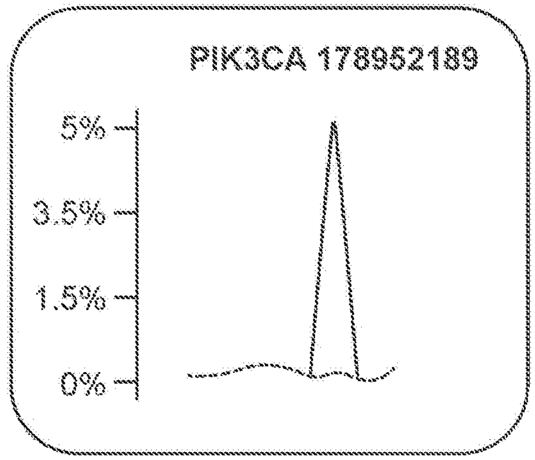
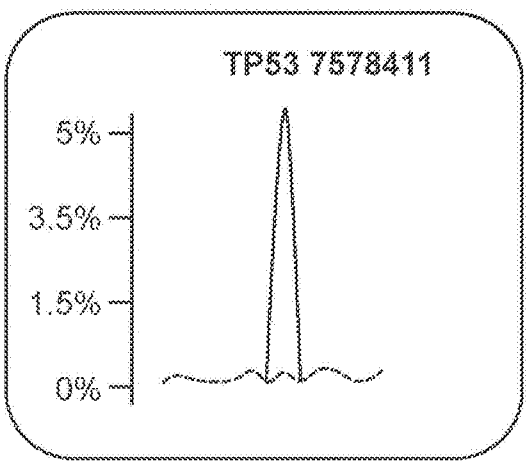
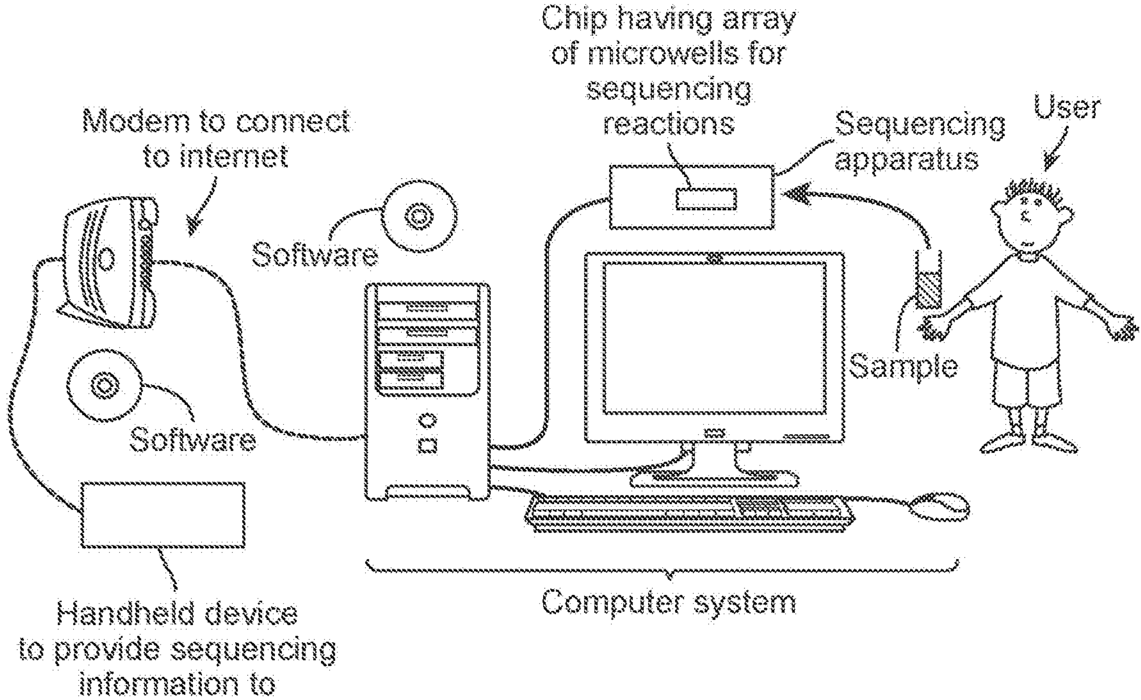
FIG. 4

| Point Mutations (SNVs) (70 Genes) | | | | | | Amplifications (CNVs) (16 Genes) | | Fusions (6 Genes) | Indels (3 Genes) |
|---|---|---|---|---|---|---|---|---|---|
| *AKT1* | *ALK* | *APC* | *AR* | *ARAF* | *ARID1A* | *AR* | *BRAF* | *ALK* | *EGFR** |
| *ATM* | *BRAF* | *BRCA1* | *BRCA2* | *CCND1* | *CCND2* | *CCNE1* | *CDK4* | *FGFR2* | *ERBB2** |
| *CCNE1* | *CDH1* | *CDK4* | *CDK6* | *CDKN2A* | *CDKN2B* | *CDK6* | *EGFR* | *FGFR3* | *MET*** |
| *CTNNB1* | *EGFR* | *ERBB2* | *ESR1* | *EZH2* | *FBXW7* | *ERBB2* | *FGFR1* | *NTRK1* | |
| *FGFR1* | *FGFR2* | *FGFR3* | *GATA3* | *GNA11* | *GNAQ* | *FGFR2* | *KIT* | *RET* | |
| *GNAS* | *HNF1A* | *HRAS* | *IDH1* | *IDH2* | *JAK2* | *KRAS* | *MET* | *ROS1* | |
| *JAK3* | *KIT* | *KRAS* | *MAP2K1* | *MAP2K2* | *MET* | *MYC* | *PDGFRA* | | |
| *MLH1* | *MPL* | *MYC* | *NF1* | *NFE2L2* | *NOTCH1* | *PIK3CA* | *RAF1* | | |
| *NPM1* | *NRAS* | *NTRK1* | *PDGFRA* | *PIK3CA* | *PTEN* | | | | |
| *PTPN11* | *RAF1* | *RB1* | *RET* | *RHEB* | *RHOA* | | | | * exons 19 & 20 |
| *RIT1* | *ROS1* | *SMAD4* | *SMO* | *SRC* | *STK11* | | | | * exons 19 & 20 |
| *TERT* | *TP53* | *TSC1* | *VHL* | | | | | | * exon 14 skipping |

FIG. 5

PREDICTIVE MODEL FOR DETERMINING CHANGES IN MOLECULAR STATE

CROSS-REFERENCE

This application is a continuation of U.S. patent application Ser. No. 18/642,389 filed Apr. 22, 2024 which is a continuation of U.S. patent application Ser. No. 18/173,361, filed Feb. 23, 2023, now allowed, which is a continuation of U.S. patent application Ser. No. 17/814,768, filed Jul. 25, 2022, now U.S. Pat. No. 11,621,083, which is a continuation of U.S. patent application Ser. No. 17/690,466, filed Mar. 9, 2022, which is a continuation of U.S. patent application Ser. No. 17/011,835, filed Sep. 3, 2020, now U.S. Pat. No. 11,282,610, which is a continuation of U.S. patent application Ser. No. 16/075,105, filed Aug. 2, 2018, now U.S. Pat. No. 11,335,463, which is a national stage application of PCT/US2017/016295, filed Feb. 2, 2017, which claims priority to U.S. Provisional Patent Application No. 62/290,375, filed Feb. 2, 2016, which is entirely incorporated herein by reference.

BACKGROUND

Cancer is a major burden of disease worldwide. Each year, tens of millions of individuals are diagnosed with cancer around the world, and more than half of such individuals may not be effectively treated for cancer and may eventually die. In many countries, cancer ranks as the second most common cause of death following cardiovascular diseases.

Drugs that target genetic vulnerabilities in human tumors have now been clinically validated as effective cancer therapies. However, the acquisition of resistance to such treatments may significantly limit their utility and remains a substantial challenge to the clinical management of advanced cancers. Resistance to treatment with anticancer drugs may result from a variety of factors, including individual variations in subjects and the emergence and expansion of genetic variants within tumors. The most common reason for acquisition of resistance to a broad range of anticancer drugs is expression of one or more energy-dependent transporters that detect and eject anticancer drugs from cells, but other mechanisms of resistance may include insensitivity to drug-induced apoptosis and induction of drug-detoxifying mechanisms.

The development of resistance to chemotherapy is a frequent, often lethal consequence for cancer patients with solid tumors—such as those of the breast, prostate, lung and colon—that have metastasized, or spread, throughout the body. In some cases, specific mutational mechanisms contribute directly to acquired drug resistance, and in other cases it appears that non-mutational and possibly epigenetic mechanisms play a significant role.

The gold standard for mechanistic characterization of tumor drug resistance involves detailed studies of tumor tissue obtained before treatment and after relapse together with experimental confirmation of candidate resistance effectors.

SUMMARY

As recognized herein, there exists a considerable need for alternative tools to predict patient response and emerging resistance to cancer treatment.

The present disclosure provides methods and systems for detecting or monitoring cancer evolution. Such methods and systems may be used for predicting patient response and emerging resistance to cancer treatment, as well as other advantages.

In one aspect, the present disclosure provides for a computer-implemented method, comprising: (a) obtaining information about a plurality of subjects with cancer at a first time point, wherein the information comprises for each subject of the plurality of subjects at least a genetic profile of a tumor obtained by genotyping nucleic acids from a cell-free bodily fluid and any treatment provided to the subject before the first time point, and determining a first state of each of the plurality of subjects based on the information at the first time point to produce a set of first states; (b) obtaining the information about the plurality of subjects at one or more second time points subsequent to the first time point, and determining a second state of each of the plurality of subjects at each of the one or more second time points based on the information at a given one of the one or more second time points, to produce a set of subsequent states; and (c) using the set of first states from (a) and the set of subsequent states from (b) to generate a predictive algorithm that is configured to determine a probability that a given first state will result in a second state among a set of states at a later time point subsequent to the given first state. In some embodiments, the method further comprises (d) for the given first state among a set of states at an earlier time point, determining the probability that the given first state will result in the second state among the set of states at the later time point; and (e) generating an electronic output indicative of the probability determined in (d).

In one aspect, the present disclosure provides for a computer-implemented method, comprising: (a) obtaining information about a plurality of subjects with cancer at a first time point, wherein the information comprises, for each subject of the plurality of subjects, at least a genetic profile of a tumor obtained by genotyping at least 50 genes and any treatment provided to the subject before the first time point, and determining a first state of each of the plurality of subjects based on the information at the first time point, to produce a set of first states; (b) obtaining the information about the plurality of subjects at one or more second time points subsequent to the first time point, and determining a second state of each of the plurality of subjects at each of the one or more second time points based on the information at a given one of the one or more second time points, to produce a set of subsequent states; and (c) using the set of first states from (a) and the set of subsequent states from (b) to generate a predictive algorithm that is configured to determine a probability that a given first state will result in a second state among a set of states at a later time point subsequent to the given first state. In some embodiments, the method further comprises (d) for the given first state among a set of states at an earlier time point, determining the probability that the given first state will result in the second state among the set of states at the later time point; and (e) generating an electronic output indicative of the probability determined in (d).

In some embodiments, obtaining the information comprises sequencing cell-free deoxyribonucleic acid (cfDNA) from the plurality of subjects and, optionally, performing a medical interview of each of the plurality of subjects. In some embodiments, treatment was provided to the subject before the first time point. In some embodiments, the methods comprise generating one or more decision trees, each decision tree comprising a root node, one or more decision branches, one or more decision nodes, and one or more terminal nodes, wherein a state at the root node represents the first time point, the one or more decision branches represent alternative treatments, and the one or more decision nodes and the one or more terminal nodes represent subsequent states. In some embodiments, the one or more decision branches comprise a plurality of decision branches. In some embodiments, the subsequent states comprise a viability state(s) of the subjects indicative of the subjects being alive or deceased. In some embodiments, the subsequent states comprise a subject survival rate. In some embodiments, each of the first states comprises a common set of one or more somatic mutations. In some embodiments, the information further comprises a subject profile.

In some embodiments, the probability is at least in part a function of treatment choice from among a plurality of treatment choices. In some embodiments, the one or more second time points comprises a plurality of subsequent time points. In some embodiments, the methods further comprise determining the probability at a plurality of subsequent time points. In some embodiments, the time points comprise at least three time points or at least four time points. In some embodiments, the first time point is prior to the subject receiving the treatment and the subsequent time point is after the subject receiving the treatment. In some embodiments, a second treatment is administered after the subsequent time point based on the subsequent state at the subsequent time point.

In some embodiments, the information about the plurality of subjects comprises one or more characteristics from patient profiles of the subjects, which characteristics are selected from the group consisting of: age, sex, gender, genetic profile, enzyme levels, organ function, quality of life, frequency of medical interventions, remission status, and patient outcome. In some embodiments, the genetic profile comprises a genotype of a subject at one or more loci that increases cancer risk, impacts pharmacokinetics, or impacts drug sensitivity. In some embodiments, the information about the plurality of subjects comprises one or more characteristics from tumor profiles of the subjects, which characteristics are selected from the group consisting of: one or more genetic variants, tissue of origin, tumor burden, tumor drug sensitivity, and tumor stage. In some embodiments, the one or more characteristics are determined by assaying cell-free nucleic acid molecules from the subjects. In some embodiments, the one or more genetic variants are quantified to determine a proportion of cell-free nucleic acid molecules comprising the one or more somatic mutations. In some embodiments, the methods further comprise determining if the proportion of the one or more somatic mutations is increasing or decreasing between the first time point and the one or more subsequent time points. In some embodiments, the methods, further comprise determining if the proportion of the one or more somatic mutations is increasing or decreasing amongst a plurality of the one or more subsequent time points. In some embodiments, the proportion of the one or more somatic mutations is increasing. In some embodiments, the one or more somatic mutations is increasing, and further wherein the somatic mutations are associated with resistance to the treatment. In some embodiments, the assaying comprises high-throughput sequencing.

In another aspect, the present disclosure provides a method, comprising: (a) obtaining information about a subject with a cancer at a first time point, wherein the information comprises at least one characteristic of the subject from a patient profile, a tumor profile, or a treatment; (b) determining an initial state of the subject based on the information at the first time point; (c) determining a probability for each of a plurality of subsequent states at each of one or more subsequent time points based on the initial state of the subject, thereby providing a set of probabilities with regards to state outcomes; (d) generating a recommendation of a treatment for the cancer based at least in part on the set of probabilities with regards to state outcomes that optimizes for a probability that subject obtains a particular outcome; and (e) generating an electronic output indicative of the recommendation generated in (d). In some embodiments, the probability is at least in part a function of a treatment choice from among a plurality of treatment choices. In some embodiments, the one or more subsequent time points comprises a plurality of subsequent time points. In some embodiments, the method further comprises determining the probability at a plurality of subsequent time points. In some embodiments, the time points comprise at least three time points. In some embodiments, the time points comprise at least four time points. In some embodiments, the first time point is prior to the subject receiving the treatment and the subsequent time point is after the subject receiving the treatment. In some embodiments, a second treatment is administered after the subsequent time point based on the subsequent state at the subsequent time point. In some embodiments, the at least one characteristic of the subject is from the patient profile and is selected from the group consisting of: age, gender, genetic profile, enzyme levels, organ function, quality of life, frequency of medical interventions, remission status, and patient outcome.

In some embodiments, the genetic profile comprises a genotype of a subject at one or more loci that is a heritable oncogene. In some embodiments, the genetic profile comprises a genotype of a subject at one or more loci that impacts pharmacokinetics. In some embodiments, the genetic profile comprises a genotype of a subject at one or more loci that impacts drug sensitivity. In some embodiments, the at least one characteristic of the subject is from the tumor profile and is selected from the group consisting of: one or more somatic mutations, tissue of origin, tumor burden, tumor drug sensitivity, and tumor stage. In some embodiments, the at least one characteristic is determined by assaying cell-free nucleic acid molecules from the subject.

In some embodiments, the somatic mutations are quantified to determine a proportion of cell-free nucleic acid molecules derived from the tumor comprising the one or more somatic mutations.

In some embodiments, the method further comprises determining if the proportion of the one or more somatic mutations is increasing or decreasing between the first time point and the one or more subsequent time points. In some embodiments, the method further comprises determining if the proportion of the one or more somatic mutations is increasing or decreasing amongst a plurality of the one or more subsequent time points. In some embodiments, the assaying comprises high-throughput sequencing. In some embodiments, the tumor profile is not derived from a tumor tissue biopsy.

In one aspect, the present disclosure provides a method, comprising: (a) obtaining information about a subject comprising at least a genetic profile of a tumor and a treatment previously or currently provided to the subject, if any, and determining an initial state of the subject based on the information; (b) providing a decision tree, wherein a root node represents an initial subject state, decision branches represent alternative treatments available to the subject, chance nodes represent points of uncertainty, and decision nodes or terminal nodes represent subsequent states; (c) providing a course of treatment for the subject that maximizes a probability of the subject achieving a living state at a terminal node; and (d) generating an electronic output indicative of the course of treatment determined in (c).

In one aspect, the present disclosure provides a method, comprising: (a) establishing one or more communications links over a communication network with one or more medical service providers; (b) receiving over the communications network from the one or more medical service providers medical information about one or more subjects; (c) receiving from the medical service provider one or more samples comprising cell-free deoxyribonucleic acid (cfDNA) from each of the one or more subjects; (d) sequencing the cfDNA and identifying one or more genetic variants present in the cfDNA; (e) creating or supplementing a database with information for each of the one or more subjects, the information comprising both identified genetic variants and received medical information; and (f) using the database and a computer implemented algorithm, generating at least one predictive model that predicts, based on an initial state of a subject, the probability of a subsequent state for each of a plurality of different therapeutic interventions.

In one aspect, the present disclosure provides a non-transitory computer-readable medium comprising machine executable code that, upon execution by one or more computer processors, implements a method comprising: (a) obtaining information about a plurality of subjects with cancer at a first time point, wherein the information comprises, for each subject of the plurality of subjects, at least a genetic profile of a tumor obtained by genotyping nucleic acids from a cell-free bodily fluid and any treatment provided to the subject before the first time point, and determining a first state of each of the plurality of subjects based on the information at the first time point, to produce a set of first states; (b) obtaining the information about the plurality of subjects at one or more second time points subsequent to the first time point, and determining a second state of each of the plurality of subjects at each of the one or more second time points based on the information at a given one of the one or more second time points, to produce a set of subsequent states; and (c) using the set of first states from (a) and the set of subsequent states from (b) to generate a predictive algorithm that is configured to determine a probability that a given first state will result in a second state among a set of states at a later time point subsequent to the given first state.

In one aspect, the present disclosure provides a non-transitory computer-readable medium comprising machine executable code that, upon execution by one or more computer processors, implements a method comprising: (a) obtaining information about a plurality of subjects with cancer at a first time point, wherein the information comprises, for each subject of the plurality of subjects, at least a genetic profile of a tumor obtained by genotyping at least 50 genes and any treatment provided to the subject before the first time point, and determining a first state of each of the plurality of subjects based on the information at the first time point, to produce a set of first states; (b) obtaining the information about the plurality of subjects at one or more second time points subsequent to the first time point, and determining a second state of each of the plurality of subjects at each of the one or more second time points based on the information at a given one of the one or more second time points, to produce a set of subsequent states; and (c) using the set of first states from (a) and the set of subsequent states from (b) to generate a predictive algorithm that is configured to determine a probability that a given first state will result in a second state among a set of states at a later time point subsequent to the given first state.

In one aspect, the present disclosure provides a method, comprising: (a) obtaining information about a subject comprising at least a genetic profile of a tumor and a treatment previously or currently provided to the subject, if any, and determining an initial state of the subject based on the information; (b) providing a decision tree, wherein a root node represents an initial subject state, decision branches represent alternative treatments available to the subject, chance nodes represent points of uncertainty, and decision nodes or terminal nodes represent subsequent states; (c) providing a course of treatment for the subject that maximizes a probability of the subject achieving a living state at a terminal node; and (d) administering the course of treatment to the subject. In some embodiments, the method further comprises: (e) at a second time point subsequent to the initial state, obtaining information about a subject comprising at least a genetic profile of a tumor and a treatment previously or currently provided to the subject, if any, and determining an second state of the subject among a plurality of subsequent states based on the information; (f) based on the second state, providing a subsequent course of treatment for the subject that maximizes probability of the subject achieving a living state at a terminal node; and (g) administering the subsequent course of treatment to the subject. In some embodiments, the method further comprises: (e) at a second time point subsequent to the initial state, obtaining information about a subject comprising at least a genetic profile of a tumor and a treatment previously or currently provided to the subject, if any, and determining an second state of the subject among a plurality of subsequent states based on the information; (f) based on the second state, providing a subsequent course of treatment for the subject that maximizes probability of the subject achieving a living state at a terminal node; and (g) administering the subsequent course of treatment to the subject.

In one aspect, the present disclosure provides a method, comprising providing a course of treatment among a plurality of alternative treatments for a subject with cancer, wherein the subject has been characterized by a decision tree comprising a plurality of decision branches, each decision branch representing an alternative treatment among the plurality of alternative treatments, which course of treatment maximizes a probability of the subject achieving a living state at a terminal node.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows an exemplary method for analyzing mutations in various disease states of a subject.

FIG. 4 shows a schematic representation of internet-enabled access of reports of a subject with cancer.

FIG. 5 shows a plurality of genes associated with genetic variants.

DETAILED DESCRIPTION

Figure 2A:
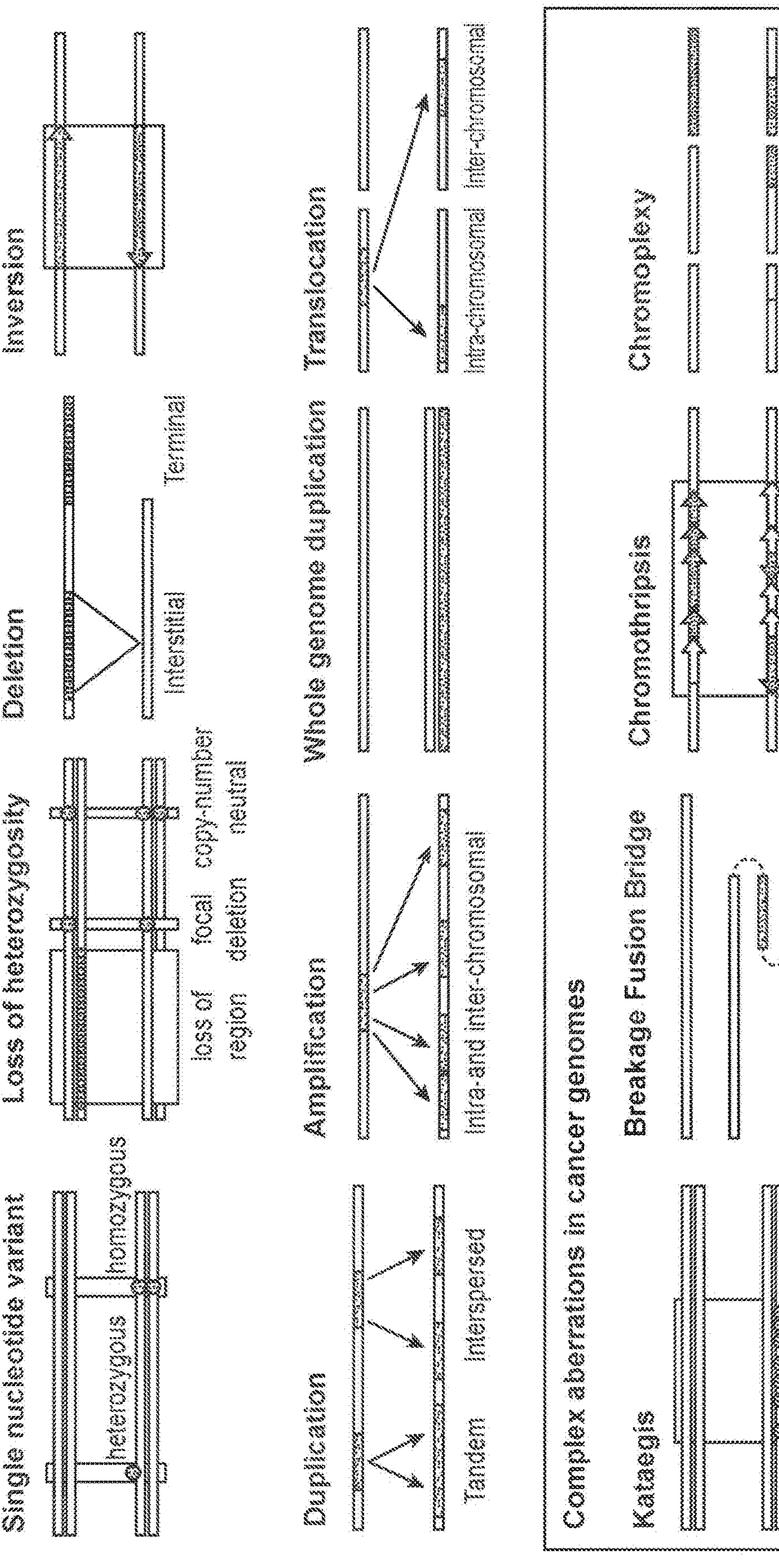
FIG. 2A shows various common aberrations in cancer genomes.

Genetic variants are alternative forms at a genetic locus. In the human genome, approximately 0.1% of nucleotide positions are polymorphic, that is, exist in a second genetic form occurring in at least 1% of the population. Mutations can introduce genetic variants into the germ line, and also into disease cells, such as cancer. Reference sequences, such as hg19 or NCBI Build 37 or Build 38, intend to represent a "wild type" or "normal" genome. However, to the extent they have a single sequence, they do not identify common polymorphisms which may also be considered normal.

Genetic variants include sequence variants, copy number variants, and nucleotide modification variants. A sequence variant is a variation in a genetic nucleotide sequence. A copy number variant is a deviation from wild type in the number of copies of a portion of a genome. Genetic variants include, for example, single nucleotide variations (SNPs), insertions, deletions, inversions, transversions, translocations, gene fusions, chromosome fusions, gene truncations, copy number variations (e.g., aneuploidy, partial aneuploidy, polyploidy, gene amplification), abnormal changes in nucleic acid chemical modifications, abnormal changes in epigenetic patterns, and abnormal changes in nucleic acid methylation.

The term "polynucleotide," as used herein, generally refers to a molecule comprising one or more nucleic acid subunits. A polynucleotide can include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be an A, C, G, T, or U, or any other subunit that is specific to one or more complementary A, C, G, T, or U, or complementary to a purine (i.e., A or G, or variant thereof) or a pyrimidine (i.e., C, T, or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a polynucleotide is deoxyribonucleic acid (DNA) or ribonucleic acid (RNA), or derivatives thereof. A polynucleotide can be single stranded or double stranded.

The term "subject," as used herein, generally refers to an animal, such as a mammal (e.g., human) or avian (e.g., bird), or other organism, such as a plant. More specifically, the subject can be a vertebrate, a mammal, a mouse, a primate, a simian, or a human. Animals include, but are not limited to, farm animals, sport animals, and pets. A subject can be a healthy individual, an individual that has or is suspected of having a disease or a pre-disposition to the disease, or an individual that is in need of therapy or suspected of needing therapy. A subject can be a patient.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes a human genome. A "reference genome" typically refers to a haploid genome. Reference genomes include, for example, hg19 or NCBI Build 37 or Build 38.

The terms "adaptor(s)", "adapter(s)", and "tag(s)" are used synonymously throughout this specification. An adaptor or tag can be coupled to a polynucleotide sequence to be "tagged" by any approach including ligation, hybridization, or other approaches.

The term "library adaptor" or "library adapter", as used herein, generally refers to a molecule (e.g., polynucleotide) whose identity (e.g., sequence) can be used to differentiate polynucleotides in a biological sample (also "sample" herein).

The term "sequencing adaptor," as used herein, generally refers to a molecule (e.g., polynucleotide) that is adapted to permit a sequencing instrument to sequence a target polynucleotide, such as by interacting with the target polynucleotide to enable sequencing. The sequencing adaptor permits the target polynucleotide to be sequenced by the sequencing instrument. In an example, the sequencing adaptor comprises a nucleotide sequence that hybridizes or binds to a capture polynucleotide attached to a solid support of a sequencing system, such as a flow cell. In another example, the sequencing adaptor comprises a nucleotide sequence that hybridizes or binds to a polynucleotide to generate a hairpin loop, which permits the target polynucleotide to be sequenced by a sequencing system. The sequencing adaptor can include a sequencer motif, which can be a nucleotide sequence that is complementary to a flow cell sequence of other molecule (e.g., polynucleotide) and is usable by the sequencing system to sequence the target polynucleotide. The sequencer motif can also include a primer sequence for use in sequencing, such as sequencing by synthesis (SBS). The sequencer motif can include the sequence(s) needed to couple a library adaptor to a sequencing system and sequence the target polynucleotide.

As used herein the terms "at least", "at most", or "about", when preceding a series, refers to each member of the series, unless otherwise identified.

The term "about" and its grammatical equivalents in relation to a reference numerical value can include a range of values up to plus or minus 10% from that value. For example, the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

In general, methods are disclosed herein to generate a predictive model of tumor evolution over time in response to various treatments and to use the model to choose treatments for subjects (e.g., patients). The predictive model is based at least on a genetic profile of a tumor and, optionally, a patient profile and/or a treatment. The results can be disclosed to patients or healthcare providers to improve care.

In some cases, information comprises a genetic profile from a tumor obtained by genotyping a cell-free bodily fluid (e.g., cfDNA). In some cases, information further comprises treatments and/or therapeutic interventions provided to the subject. In some cases, information further comprises a subject profile.

Information can be used to determine a state associated with a subject. A state can comprise information relevant to predicting subsequent states of the subject. For example, a state can indicate that a subject is alive or deceased. A state can indicate a median life expectancy for a subject. A state can indicate medically relevant somatic mutations in the tumor (e.g., a KRAS variant). A state can indicate drug resistance (e.g., cetuximab resistance).

Information may be used to generate one or more decision trees indicating the probability of various endpoints for a subject exhibiting a particular state. Decision branches may emanate from the root node (which can be considered a first decision node). A decision branch may lead either to an endpoint (also called a terminal node) or to a chance node. A terminal node or endpoint may represent a state. A chance node (or event node) may be a point of uncertainty from which different outcomes are possible. Uncertainty may be resolved through chance branches (event branches) emanating from a chance node. Each chance branch may lead either to a terminal node or to a decision node (which, itself, can represent a state), from which a plurality of decision branches emanate. These decision branches may, in turn, lead to endpoints or to chance nodes in continuing fashion until every branch leads to an endpoint or terminal node.

A root node in a decision tree can be an initial state. The initial state can be as broad as "cancer diagnosis". More typically, the root node will indicate some aspect of a genetic profile of a subject. For example, the root node can indicate one or more genetic variants detected in cfDNA, e.g., presence of a mutant in a particular oncogene, and/or their amount relative to normal DNA. Each decision branch from the root node can represent a different course of treatment (or no treatment). For example, the course of treatment can represent different chemotherapy or immunotherapy regimens, types of surgery, or radiation. A terminal node can represent a state, for example, survival or death, e.g., within a certain time of diagnosis (for example, 5-year survival). Decision nodes represent new states, from which new decisions can be made. For example, a decision node is the emergence of a genetic variant providing chemotherapy resistance. Such variants may represent escape paths through which a tumor escapes response to the chemotherapy and which may require a different therapeutic approach.

Advantageously, methods disclosed herein can generate a predictive algorithm that is configured to determine a probability that any therapeutic intervention applied to a particular state (e.g., a particular chemotherapeutic agent for cancers with a particular genetic profile) will result in a particular state (e.g., genetic variant) from which the cancer can escape from the therapeutic intervention. Such probabilities can be determined through several rounds of treatment and escape. As a result, one can determine that particular series of therapeutic interventions lead to particular modes of escape, ultimate escape (e.g., death), or undetectability of cancer with given frequencies or probabilities.

The present disclosure provides methods of generating a predictive algorithm to assign probabilities to each branch or each terminal node in a decision tree. The methods may make use of databases in which results at each branch are calculable from a plurality of subjects for which data is stored. Probabilities can be determined, for example, by obtaining a training set of subjects, classifying them into states, recording treatments and/or therapeutic interventions, and then determining frequency of outcomes (e.g., final states). The frequency of a given outcome in the training set can be used to determine its probability.

Accordingly, for a plurality of subjects exhibiting a particular state, a plurality of decision branches may be identified, and the chance of a particular endpoint or decision node at the end of the branch may be determined. For example, referring to FIG. 6, among individuals exhibiting state "EGFR mutant", the decision branches may include Treatment A and Treatment B.

Figure 6:
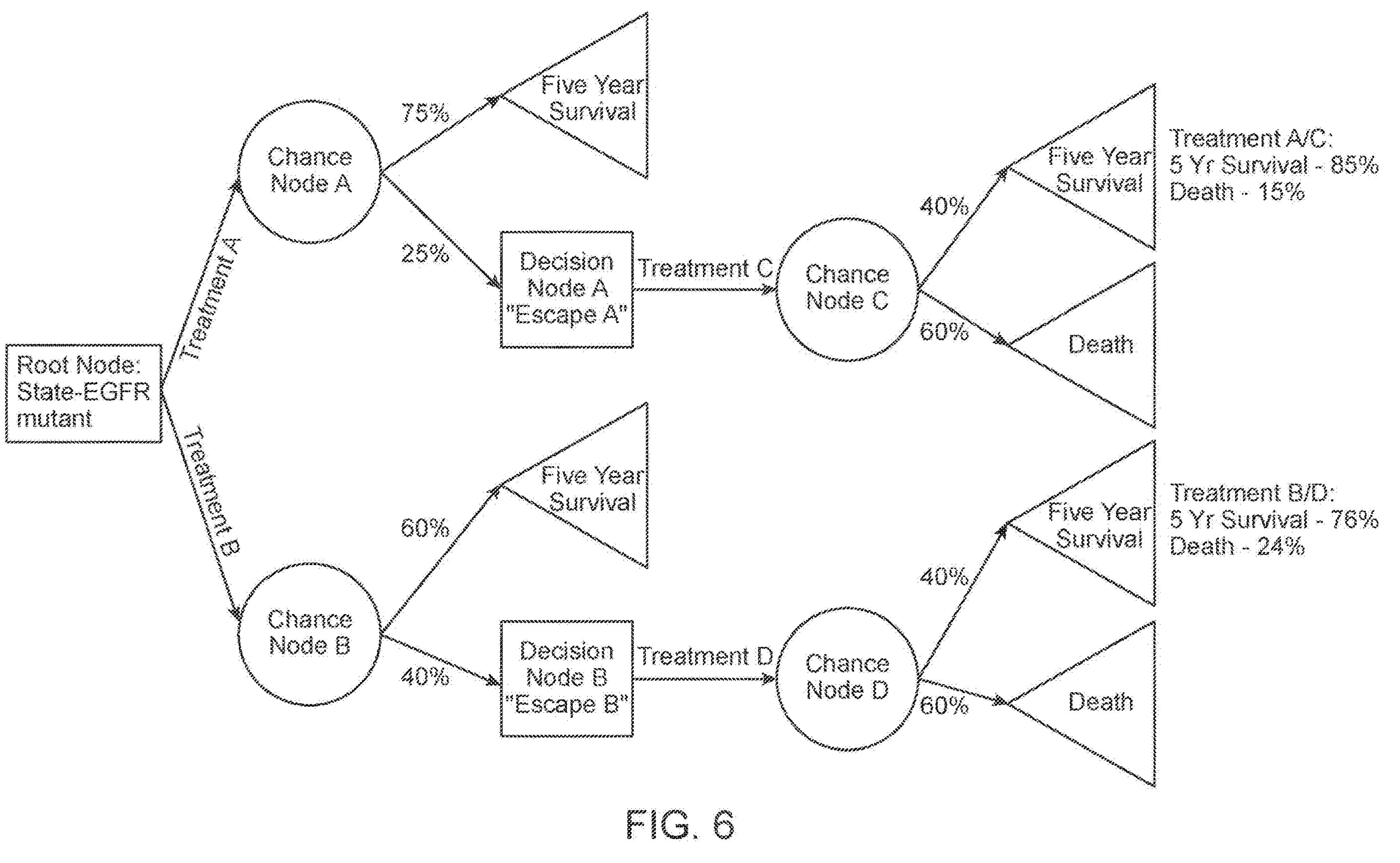
FIG. 6 shows a decision tree comprising a root node (rectangle) indicating an initial state, decision branches (arrows) indicating different therapeutic interventions, and chance nodes (circles) from which chance branches (arrows) emanate to either terminal nodes (triangles) or decision nodes (squares) indicating subsequent states.

In FIG. 6, Treatment A leads to chance node A, Treatment B leads to chance node B. Chance node A leads to 5-year survival (a terminal node) 75% of the time, and to development of "Escape A" (decision node A) 25% of the time. Escape A can have one decision branch-Treatment C. This leads to Chance node C, from which two chance branches emanate to terminal nodes: 40% five-year survival and 60% death. In sum, this branch produces 85% chance of 5-year survival and 15% chance of death.

In FIG. 6, Treatment B leads to chance node B. Chance node B leads to 5-year survival (a terminal node) 60% of the time; and to development of "Escape B" (decision node B) 40% of the time. Escape B can have one decision branch-Treatment D. This leads to Chance node D, from which two chance branches emanate to terminal nodes: 40% five-year survival and 60% death. In sum, this branch produces 76% chance of 5-year survival and 24% chance of death.

Adding more data points (subjects) at any decision node may increase the reliability of ultimate probabilities determined. In some cases, initial states can be used to predict subsequent states (e.g., intermediate states (e.g., at decision nodes) or final states). In some cases, initial states can be classified as leading to subsequent states (e.g., intermediate states or final states) with a given frequency. A subsequent state can be a state achieved after a decision from a previous state. For example, after State 1, a therapeutic intervention is applied, and a state later in time is a subsequent state. A subsequent state can be a terminal state, from which no further decision is taken, or it can be an intermediate state, from which another decision is taken.

Initial states can be determined by clustering subjects based on the information or a subset of the information determined about the subject. Information about the subjects or a training set of subjects can be used to generate the clusters. For example, information can be categorical (e.g., a KRAS variant is present or absent in a tumor sample), and subjects can be clustered based on a shared categorical value. In some cases, the information about the subject is quantitative. Subjects can be clustered using quantitative data by any method known to the art. Exemplary methods include but are not limited to k-means clustering, hierarchical clustering, or centroid-based clustering. Clustering can be based on visual inspection of data, including data that has been projected onto a reduced number of dimensions by methods such as Principle Component Analysis. Clustering can be used to create cluster boundaries, defining which clusters subjects will be placed in.

A profile includes a value (quantitative or qualitative) for each of one or more features. A profile can include information about, for example, phenotypic features, genetic features, demographic features, or medical history (including history of therapeutic interventions delivered). A genetic profile includes values regarding various genetic features, for example, genetic variants at a locus (e.g., sequence information of copy number information). For example, a genetic profile can include germline genotype at a number of loci or somatic cell genotype in pathologic (e.g., cancer) cells. A state can be one or more values of features in a profile.

Information can comprise a tumor profile, including a genetic profile of the tumor. Information can comprise a subject profile, including genetic information about the subject. Information can comprise prior treatments or therapeutic interventions the subject has undergone.

A profile of a tumor can comprise tissue of origin, tumor burden, tumor drug sensitivity, tumor stage, tumor size, a metabolic profile of the tumor, metastatic status of the tumor, tumor burden, or tumor heterogeneity.

A profile of a tumor can comprise a tumor genetic profile, which can be obtained by various methods. For example, a tumor genetic profile can be obtained by analyzing nucleic acids from a biological sample from a subject by high-throughput sequencing or a genotyping array. The nucleic acids can be DNA or RNA. The nucleic acids are isolated from a sample. The sample used to produce the genetic profile can be a tumor biopsy, a fine-needle aspirate biopsy, or a cell-free bodily fluid containing nucleic acids from the tumor cells. For example, the cell-free bodily fluid can be derived from bodily fluids selected from the group consisting of blood, plasma, serum, urine, saliva, mucosal excretions, sputum, stool, cerebral spinal fluid, and tears of the subject.

For example, blood from subjects at risk for cancer may be drawn and prepared as described herein to generate a population of cell free polynucleotides. In an example, this is cell-free DNA (cfDNA). The systems and methods of the present disclosure may be employed to detect mutations or copy number variations that may exist in certain cancers present. The method may help detect the presence of cancerous cells in the body, despite the absence of symptoms or other hallmarks of disease.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent with or without the use of an automated nucleic acid extractor, e.g., the Model 341 DNA Extractor available from Applied Biosystems (Foster City, CA); (2) stationary phase adsorption methods; and (3) salt-induced nucleic acid precipitation methods, such precipitation methods being typically referred to as "salting-out" methods. Another example of nucleic acid isolation and/or purification is the use of magnetic particles to which nucleic acids can specifically or non-specifically bind, followed by isolation of the beads using a magnet, and washing and eluting the nucleic acids from the beads. In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical properties.

The extracted polynucleotides from the samples can be sequenced to generate sequencing reads. Exemplary sequencing techniques can include, for example emulsion polymerase chain reaction (PCR) (e.g., pyrosequencing from Roche 454, semiconductor sequencing from Ion Torrent, SOLID sequencing by ligation from Life Technologies, sequencing by synthesis from Intelligent Biosystems), bridge amplification on a flow cell (e.g. Solexa/Illumina), isothermal amplification by Wildfire technology (Life Technologies), or rolonies/nanoballs generated by rolling circle amplification (Complete Genomics, Intelligent Biosystems, Polonator). Sequencing technologies like Heliscope (Helicos), SMRT technology (Pacific Biosciences), or nanopore sequencing (Oxford Nanopore) that allow direct sequencing of single molecules without prior clonal amplification may be suitable sequencing platforms. Sequencing may be performed with or without target enrichment. Exemplary genes and/or regions that can be enriched for are found in FIG. 5. Enrichment can, for example, be performed by hybridization of the nucleic acid sample or sequencing library to probes disposed on an array or attached to beads. In some cases, polynucleotides from a sample are amplified by any suitable approach (e.g., PCR) prior to and/or during sequencing.

As a non-limiting example, a sample containing initial genetic material is provided and cell-free DNA can be extracted. The sample can include target nucleic acid in low abundance. For example, nucleic acid from a normal or germline genome can predominate in a sample that also includes no more than 20%, no more than 10%, no more than 5%, no more than 1%, no more than 0.5%, or no more than 0.1% nucleic acid from at least one other genome containing genetic variation, e.g., a cancer genome, a fetal genome, or a genome from another individual or species. Next, the initial genetic material may be converted into a set of tagged parent polynucleotides and sequenced to produce sequencing reads. In some cases, these sequences reads may contain barcode information. In other examples, barcodes are not utilized. Tagging can include attaching sequence tags to molecules in the initial genetic material. Sequence tags can be selected so that all unique polynucleotides mapping to the same reference sequence have a unique identifying tag. Sequence tags can be selected so that not all unique polynucleotides mapping to the same reference have a unique identifying tag. Conversion can be performed at high efficiency, for example at least 40%, at least 50%, at least 60%, at least 70%, or at least 80% of the initial nucleic acid molecules. The set of tagged parent polynucleotides can be amplified to produce a set of amplified progeny polynucleotides. Amplification may be, for example, at least 10, 100, 1,000, or 10,000-fold. The set of amplified progeny polynucleotides is sampled for sequencing at a sampling rate so that the sequencing reads produced both (1) cover a target number of unique molecules in the set of tagged parent polynucleotides and (2) cover unique molecules in the set of tagged parent polynucleotides at a target coverage fold (e.g., 5- to 10-fold coverage of parent polynucleotides). The set of sequencing reads may be collapsed to produce a set of consensus sequences corresponding to unique tagged parent polynucleotides. Sequencing reads can be qualified for inclusion in the analysis. For example, sequencing reads that fail to meet a quality control score can be removed from the pool.

Sequencing reads can be sorted into families representing reads of progeny molecules derived from a particular unique parent molecule. For example, a family of amplified progeny polynucleotides can constitute those amplified molecules derived from a single parent polynucleotide. By comparing sequences of progeny in a family, a consensus sequence of the original parent polynucleotide can be deduced. This produces a set of consensus sequences representing unique parent polynucleotides in the tagged pool. The process may assign a confidence score for the sequence. After sequencing, reads may be assigned a quality score. A quality score may be a representation of reads that indicates whether those reads may be useful in subsequent analysis based on a threshold. In some cases, some reads are not of sufficient quality or length to perform the subsequent mapping step. Sequencing reads with a predetermined quality score (above 90% for example) may be filtered out of the data. The sequencing reads that meet a specified quality score threshold may be mapped to a reference genome, or a template sequence that is known not to contain copy number variations. After mapping alignment, sequencing reads may be assigned a mapping score. A mapping score may be a representation or reads mapped back to the reference sequence indicating whether each position is or is not uniquely mappable. In instances, reads may be sequences unrelated to copy number variation analysis. For example, some sequencing reads may originate from contaminant polynucleotides. Sequencing reads with a mapping score indicating that a sequencing read has at least 90%, 95%, 99%, 99.9%, 99.99%, or 99.999% of being mismapped (e.g., incorrectly mapped) may be filtered out of the data set. In other cases, sequencing reads assigned a mapping score less than a predetermined percentage may be filtered out of the data set.

The sequencing reads that meet a specified quality score threshold may be mapped to a reference genome, or a template sequence that is known not to contain copy number variations. After mapping alignment, sequencing reads may be assigned a mapping score. In instances, reads may be sequences unrelated to copy number variation analysis. After data filtering and mapping, the plurality of sequencing reads generates a chromosomal region of coverage. These chromosomal regions may be divided into variable length windows or bins. In some cases, each of the window regions may be sized so they contain about the same number of uniquely mappable bases. Additionally, predefined windows, known throughout the genome to be hard to sequence, or contain a substantially high GC bias, may be filtered from the data set. For example, regions known to fall near the centromere of chromosomes (i.e., centromeric DNA) are known to contain highly repetitive sequences that may produce false positive results. These regions may be filtered out. Normalization may be performed to compensate for the effects of GC content on the sequencing reads of the sample. Other regions of the genome, such as regions that contain an unusually high concentration of other highly repetitive sequences such as microsatellite DNA, may be filtered from the data set.

For an exemplary genome derived from cell-free polynucleotide sequences, the next step comprises determining read coverage for each window region. This may be performed using either reads with barcodes, or without barcodes. In cases without barcodes, the previous mapping steps may provide coverage of different base positions. Sequencing reads that have sufficient mapping and quality scores and fall within chromosome windows that are not filtered, may be counted. The number of coverage reads may be assigned a score for each mappable position. In cases involving barcodes, all sequences with the same barcode, physical properties, or combination of the two may be collapsed into one read, as they are all derived from the sample parent molecule. This step may reduce biases that may have been introduced during any of the preceding steps, such as steps involving amplification. For example, if one molecule is amplified 10 times but another is amplified 1000 times, each molecule is only represented once after collapse, thereby negating the effect of uneven amplification. Only reads with unique barcodes may be counted for each mappable position and influence the assigned score. For this reason, it is important that the barcode ligation step be performed in a manner optimized for producing the lowest amount of bias. The sequence for each base may be aligned as the most dominant nucleotide read for that specific location. Further, the number of unique molecules can be counted at each position to derive simultaneous quantification at each position. This step may reduce biases which may have been introduced during any of the preceding steps, such as steps involving amplification.

The discrete copy number states of each window region can be utilized to identify copy number variation in the chromosomal regions. In some cases, all adjacent window regions with the same copy number can be merged into a segment to report the presence or absence of copy number variation state. In some cases, various windows can be filtered before they are merged with other segments.

Methods to determine a genetic profile (e.g., a tumor or subject genetic profile) may have error rates. For example, sequencing methods can have per-base error rates of about 0.1%, about 0.5%, about 1%, or higher. In some cases, nucleic acids derived from tumor cells comprising genetic variants at a given locus are present at a fraction of total nucleic acids comprising the locus at a proportion similar to or lower than the per-base sequencing error rate. In such situations, it can be difficult to distinguish between genotyping or sequencing errors and genetic variants present at a low frequency. Certain methodologies, such as those described in WO 2014/149134, which is incorporated by reference in its entirety, can be performed to reduce the error rate.

The tumor genetic profiles can comprise somatic mutations relative to a reference. The reference can be a reference genome, such as the human reference genome. The reference genome can be the subject's germline genome. The genetic profile can comprise various genetic variants acquired by some or all of the tumor cells. Genetic variants can, for example, be single-nucleotide variants, gross or small structural variants, or short insertions or deletions. For example, as shown in FIG. 2A, common aberrations in cancer genomes can lead to the abnormal chromosome numbers (aneuploidy) and chromosome structures of a cancer genome. In FIG. 2A, lines indicate the genome with germline genome on top and cancer genome with somatic aberrations below. Double lines are used when differentiating heterozygous and homozygous changes is useful. Dots represent single nucleotide changes, whereas lines and arrows represent structural changes.

The tumor genetic profile can comprise quantitative information about each variant. For example, genetic analysis of cell-free DNA by digital sequencing may produce 1,000 reads mapping to a first oncogene locus, of which 900 reads correspond to germline sequence and 100 reads correspond to variant present in the tumor cells. The same genetic analysis may produce 1,000 reads mapping to a second oncogene locus, of which 980 reads correspond to germline sequence and 20 reads corresponding to a variant indicating a tumor burden of 10%. One can infer that the overall tumor burden is about 10% in the cell-free DNA based on the first oncogene locus, but that a small fraction of tumor cells (about 20%) may have a variant at the second oncogene locus. Such quantitative information can be included in the tumor genetic profile and monitored over time or in response to a treatment.

Tumor genetic profiles can include information about somatic variants. These may include, but are not limited to, mutations, indels (insertions or deletions), copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation, infection, and cancer.

In some cases, genotyping comprises genotyping nucleic acids from a cell-free bodily fluid. Such methods can capture genetic information from a plurality of tumor cells, allowing information about both tumor heterogeneity and tumor evolution to be inferred. In some cases, the genotyping can be performed on samples provided from at least one time point, at least two time points, at least three time points, at least four time points, at least five time points, at least six time points, at least seven time points, at least eight time points, at least nine time points, or at least ten time points. In some cases, the genotyping comprises determining the genotype of at least 50, 55, 60, 65, 70, 75, 80, 85, 90, 95, 100, 120, 140, 160, 180, or 200 or more genetic loci. In some cases, genetic loci are genes. In some cases, genetic loci are oncogenes. Oncogenes are genes that comprise mutations that drive tumor growth. Exemplary oncogenes can be found in WO2009045443, which is hereby incorporated by reference in its entirety. Oncogenes can comprise genes listed in FIG. 5.

In some cases, the tumor genetic profile can comprise information about tumor evolution. For example, if a KRAS mutation is present in an increasing proportion of the tumor-derived cell-free DNA, it can be inferred that the proportion of tumor cells resistant to particular treatments targeting KRAS is increasing over time. FIG. 1 shows an exemplary method developing a model of tumor evolution in response to a treatment. The process of FIG. 1 includes collecting genetic profile data of a plurality of subjects' tumors and tumor treatment(s) (10) and original treatments. The genetic profiles may be used to identify or infer evolutionary escape paths taken by the tumor cells that lead to resistance to the treatment (12). An individual subject's tumor genetic profile can be fitted to the model to provide a probability of tumor cells acquiring genetic variants that produce resistance to treatments (14).

Figure 2B:
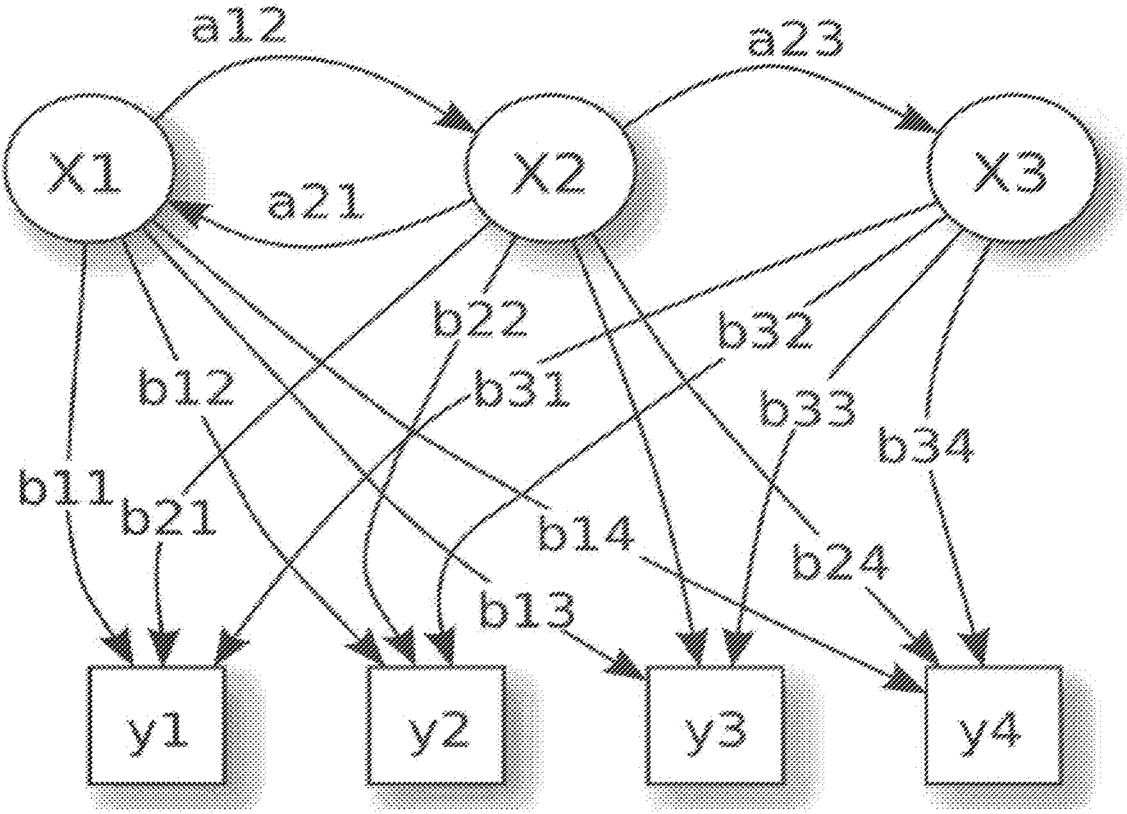
FIG. 2B shows an exemplary system to detect the evolutionary paths of escape.

More complex models can be used to measure tumor heterogeneity based on, for example, the relative prevalence of different variants in cell-free DNA. FIG. 2B shows an exemplary system to determine the probability of various state outcomes. The system can be a Hidden Markov model (HMM), which is a statistical Markov model in which the system being modeled is assumed to be a Markov process with unobserved (hidden) states. In a simple Markov models (like a Markov chain), the state is directly visible to the observer, and therefore the state transition probabilities are the only parameters. In a hidden Markov model, the state is not directly visible, but output, dependent on the state, is visible. Each state has a probability distribution over the possible output tokens. Therefore the sequence of tokens generated by an HMM may give some information about the sequence of states. A hidden Markov model can be considered a generalization of a mixture model where the hidden variables (or latent variables), which control the mixture component to be selected for each observation, are related through a Markov process rather than independent of each other. As shown in FIG. 2B, an HMM is typically defined by a set of hidden states, a matrix of state transition probabilities, and a matrix of emission probabilities. General methods to construct such models include, but are not limited to, Hidden Markov Models (HMM), artificial neural networks, Bayesian networks, support vector machines, and Random Forest. Such methods are known to one of ordinary skill in the art and are described in detail in Mohri et al., Foundations of Machine Learning, published by MIT Press (2012), which is hereby incorporated by reference in its entirety, and in MacKay, Information Theory, Inference, and Learning Algorithms, published by Cambridge University Press (2003), which is hereby incorporated by reference in its entirety.

The relative amount of tumor polynucleotides in a sample of cell free polynucleotides is referred to herein as "tumor burden." Tumor burden can be related to tumor size. Tested over time, tumor burden can be used to determine whether a cancer is advancing, stabilized or in remission. In some embodiments, the confidence intervals of the inferred tumor burden do not overlap, indicating the direction of disease progression. Tumor burdens and direction of disease progression can have a diagnostic confidence indication. The term "diagnostic confidence indication" as used herein refers to a representation, a number, a rank, a degree or a value assigned to indicate the presence of a genetic variant and how much that presence is trusted. For example, the representation can be a binary value or an alphanumeric ranking from A-Z, among others. In yet another example, the diagnostic confidence indication can have any value from 0 to 100, among others. In yet another example, the diagnostic confidence indication can be represented by a range or degree, e.g., "low" or "high", "more" or "less", "increased" or "decreased". A low diagnostic confidence indication may mean that the presence of the genetic variant cannot be trusted too much (the genetic variant may be noise). A high diagnostic confidence indication may mean that genetic variant is likely to exist and one embodiment considers a result untrusted if its diagnostic confidence indication is under 25-30 out of 100.

In one implementation, using measurements from a plurality of samples collected substantially at once or over a plurality of time points, a diagnostic confidence indication for each variant can be adjusted to indicate a confidence of predicting the observation of the copy number variation (CNV) or mutation. The confidence can be increased by using measurements at a plurality of time points to determine whether cancer is advancing, in remission or stabilized. The diagnostic confidence indication can be assigned by any of a number of known statistical methods is assigned and can be based, at least in part, on the frequency at which the measurements are observed over a period of time. For example, a statistical correlation of current and prior results can be done. Alternatively, for each diagnosis, a hidden Markov model can be built, such that a maximum likelihood or maximum a posteriori decision can be made based on the frequency of occurrence of a particular test event from a plurality of measurements or a time points. As part of this model, the probability of error and resultant diagnostic confidence indication for a particular decision can be output as well. In this manner, the measurements of a parameter, whether or not they are in the noise range, may be provided with a confidence interval. Tested over time, one can increase the predictive confidence of whether a cancer is advancing, stabilized or in remission by comparing confidence intervals over time. Two time points can be separated by about a month to about a year, about a year to about 5 years, or no more than about three months.

Figure 2C:
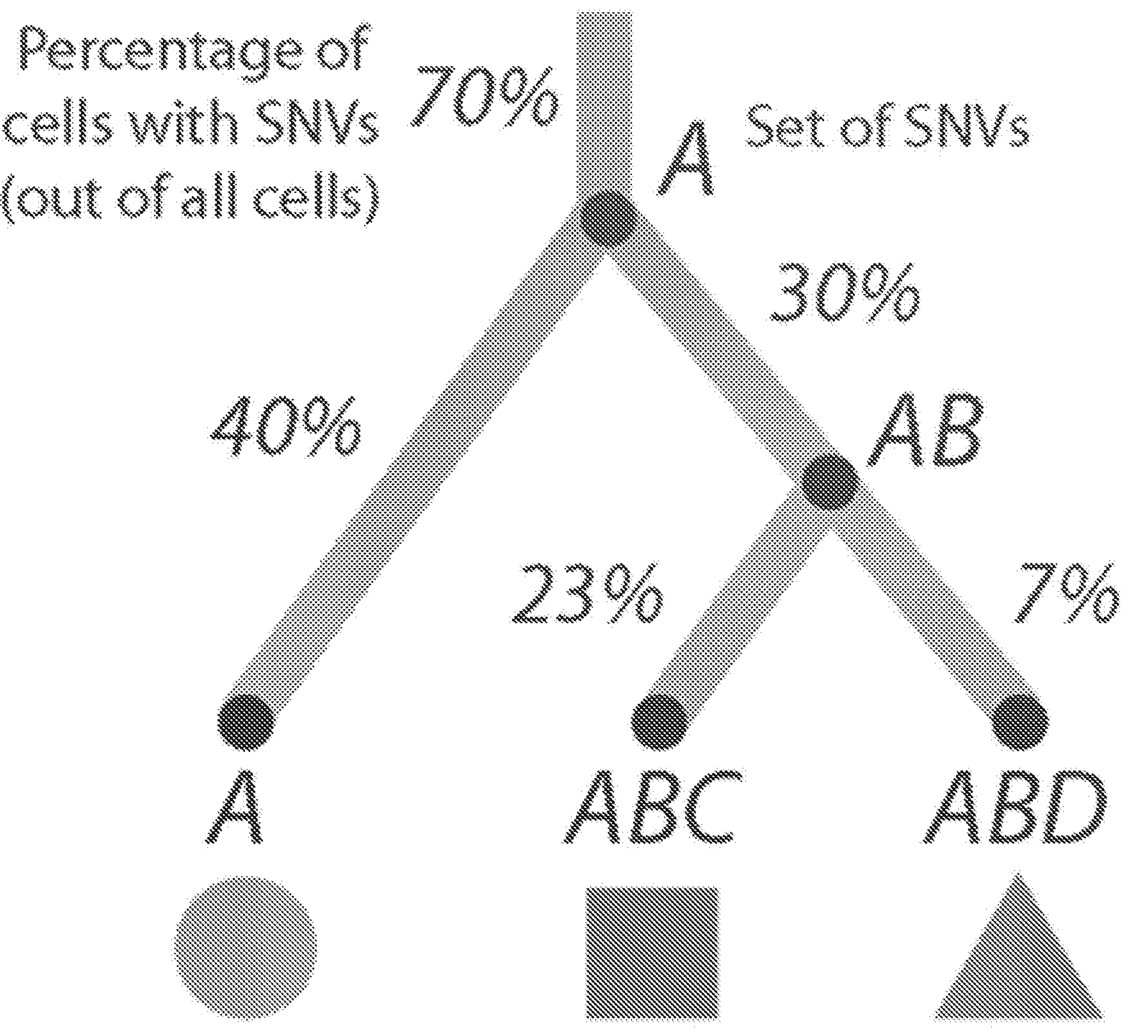
FIG. 2C shows an exemplary model generated by the system of FIG. 2B.

FIG. 2C shows an exemplary model generated by the system of FIG. 2B for inferring tumor phylogeny from next-generation sequencing data. The subclones are related to each other by an evolutionary process of acquisition of mutations. In this example, the three clones (leaf nodes) are characterized by different combinations of the four single nucleotide variant (SNV) sets A, B, C, and D. The percentages on the edges of the tree indicate the fraction of cells with this particular set of SNVs, e.g., 70% of all cells carry A, 40% additionally carry B, and only 7% carry A, B, and D.

Figure 2D:
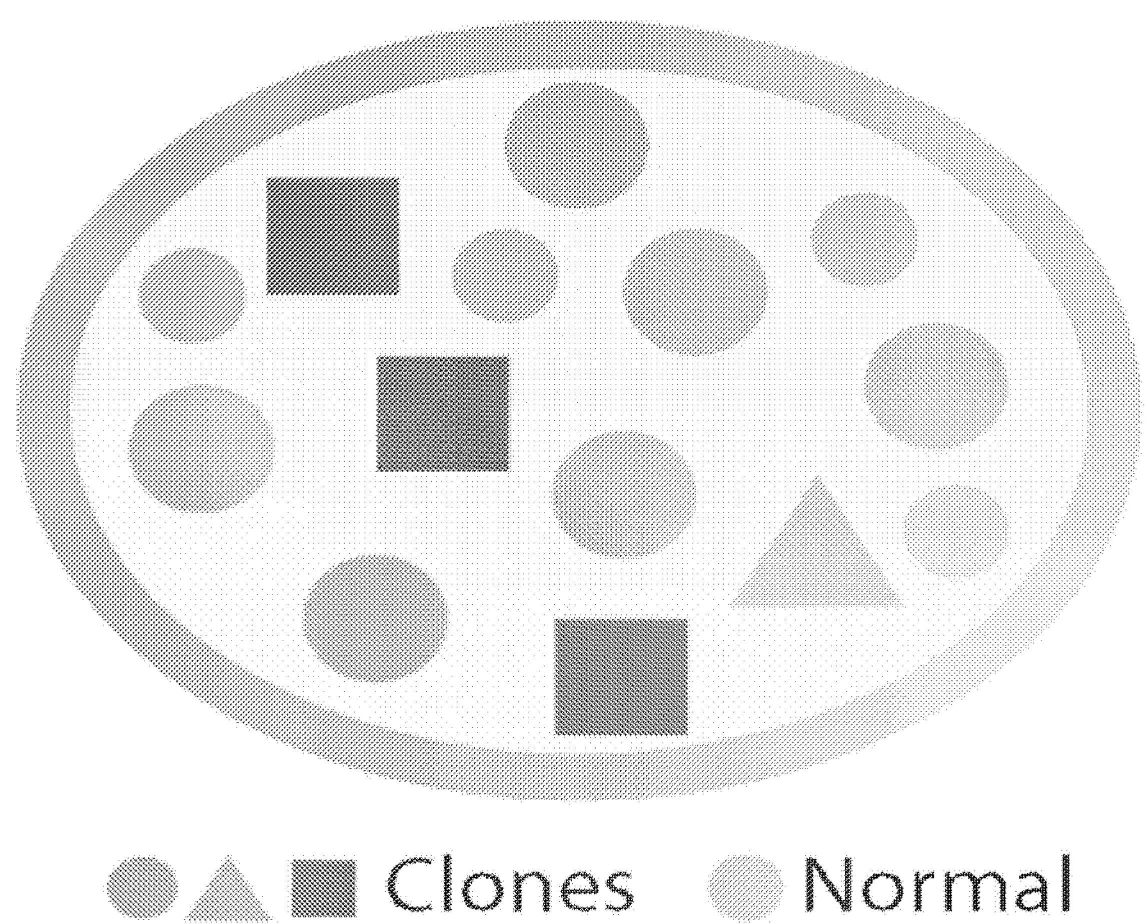
FIG. 2D shows an exemplary a heterogeneous collection of normal cells and cancer subclones developed during an evolutionary history of a tumor.

FIG. 2D shows an exemplary a heterogeneous collection of normal cells and cancer subclones developed during an evolutionary history of a tumor. The evolutionary history of a tumor gives rise to a heterogeneous collection of normal cells (small discs) and cancer subclones (large discs, triangles, squares). Internal nodes that have been fully replaced by their descendants (like the one carrying SNV sets A and B without C or D) are no longer part of the tumor.

A partnership can be established between a medical prognosis provider and one or more medical service providers, such as doctors, hospitals, medical insurers (e.g., Blue Cross), or a managed care organization (e.g., Kaiser Permanente). Medical service providers can provide to the medical prognosis provider one or more subject samples comprising cfDNA and one or more medical records including medical information in addition to, or other than, genetic information about the subject. Medical information can be provided through a secure communication link allowing the medical prognosis provider to access medical records. The medical prognosis provider can sequence (or have sequenced) cfDNA from the sample, and create a medical record that includes information to be used in the methods of the present disclosure. The medical service providers can provide new samples comprising cfDNA and/or update the information subjects pass decision nodes. Predictive models can be iteratively updated as new information becomes available.

Figure 3:
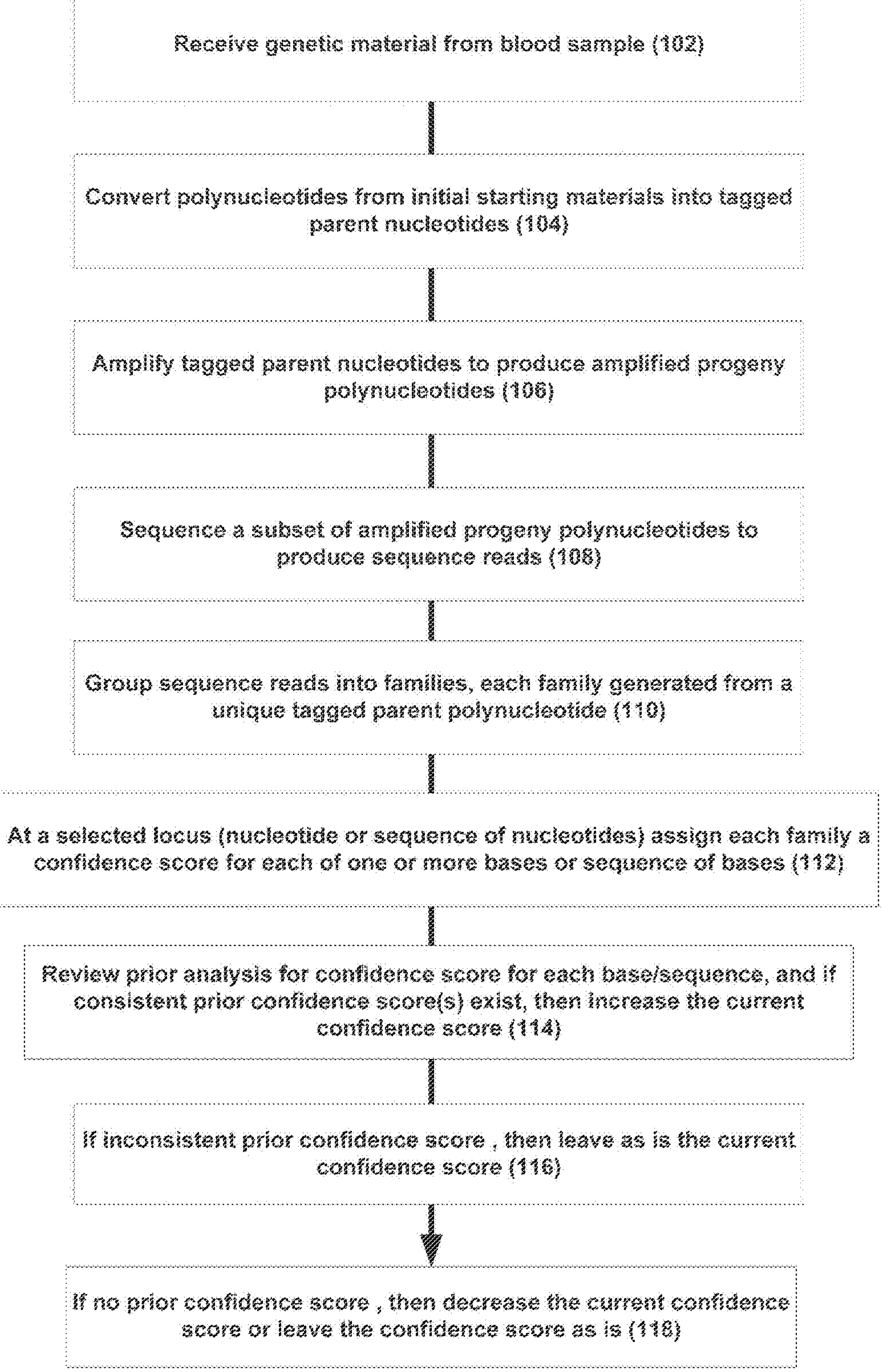
FIG. 3 shows an exemplary process to reduce error rates and bias in deoxyribonucleic acid (DNA) sequence readings.

An overview of the process of determining a genetic profile is provided in FIG. 3. The process receives genetic materials from blood sample or other body samples (102). The process converts the polynucleotides from the genetic materials into tagged parent nucleotides (104). The tagged parent nucleotides are amplified to produce amplified progeny polynucleotides (106). A subset of the amplified polynucleotides is sequenced to produce sequencing reads (108), which are grouped into families, each generated from a unique tagged parent nucleotide (110). At a selected locus, the process assigns each family a confidence score for each family (112). Next, a consensus is determined using prior readings. This is done by reviewing prior confidence score for each family, and if consistent prior confidence scores exists, then the current confidence score is increased (114). If there are prior confidence scores, but they are inconsistent, the current confidence score is not modified in one embodiment (116). In other embodiments, the confidence score is adjusted in a predetermined manner for inconsistent prior confidence scores. If this is a first time the family is detected, the current confidence score can be reduced as it may be a false reading (118). The process can infer the frequency of the family at the locus in the set of tagged parent polynucleotides based on the confidence score (120).

While temporal information can enhance the information for mutation or copy number variation detection, other consensus methods can be applied. In other embodiments, the historical comparison can be used in conjunction with other consensus sequences mapping to a particular reference sequence to detect instances of genetic variation. Consensus sequences mapping to particular reference sequences can be measured and normalized against control samples. Measures of molecules mapping to reference sequences can be compared across a genome to identify areas in the genome in which copy number varies, or heterozygosity is lost. Consensus methods include, for example, linear or non-linear methods of building consensus sequences (such as voting, averaging, statistical, maximum a posteriori or maximum likelihood detection, dynamic programming, Bayesian, hidden Markov or support vector machine methods, etc.) derived from digital communication theory, information theory, or bioinformatics. After the sequence read coverage has been determined, a stochastic modeling algorithm is applied to convert the normalized nucleic acid sequence read coverage for each window region to the discrete copy number states. In some cases, this algorithm may comprise one or more of the following: Hidden Markov Model, dynamic programming, support vector machine, Bayesian network, trellis decoding, Viterbi decoding, expectation maximization, Kalman filtering methodologies, and neural networks.

After this, a report can be generated. For example, the copy number variation (CNV) may be reported as a graph indicating various positions in the genome and a corresponding increase or decrease or maintenance of copy number variation at each respective position. Additionally, copy number variation may be used to report a percentage score indicating how much disease material (or nucleic acids having a copy number variation) exists in the cell-free polynucleotide sample.

FIG. 4 shows a schematic representation of internet-enabled access of reports of a subject with cancer. The system of FIG. 4 can use a handheld DNA sequencer or a desktop DNA sequencer. The DNA sequencer is a scientific instrument used to automate the DNA sequencing process. Given a sample of DNA, a DNA sequencer is used to determine the order of the four bases: adenine, guanine, cytosine, and thymine. The order of the DNA bases is reported as a text string, called a read. Some DNA sequencers can be also considered optical instruments as they analyze light signals originating from fluorochromes attached to nucleotides.

A tumor profile can comprise information about the tissue of origin of the tumor. The types and number of cancers that may be detected and profiled include but are not limited to blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors, and the like.

A tumor profile can comprise information about tumor drug sensitivity. Tumor drug sensitivity can be determined directly by measuring or determining a response of isolated tumor cells to the drug of interest. Tumor drug sensitivity can be determined by genotyping the tumor.

A tumor profile can comprise information about tumor size and/or tumor stage. Tumor size can be measured by body scanning technologies, by surgery, or any known method. Tumor stage can be determined based on physical exams, imaging studies, laboratory tests, pathology reports, and/or surgical reports.

A subject profile can comprise a subject genetic profile. A genetic profile of the subject can be determined by assaying non-cancerous tissue from the subject. A genetic profile of the subject can be determined by assaying nucleic acids derived from cell-free bodily fluids from the subject. The nucleic acids from the non-cancerous tissue can be identified, for example, by their frequency in the pool of initial nucleic acids or by the length of the nucleic acid molecules. Nucleic acid molecules derived from tumor cells may have a first mode between 160 and 180 bases, and a second mode between 320 and 360 bases. Nucleic acid molecules derived from non-cancerous tissue can have a wider distribution, with many molecules larger than 400 bases in length. The size of the molecules can be controlled by size selection of the initial DNA molecules or library fragments, or it can be controlled informatically by mapping paired-reads to a reference genome.

The subject genetic profile can include assaying for variants that can alter the effects of treatments. For example, such variants can affect pharmacokinetics of drugs. Common variants that affect pharmacokinetics can impact drug transport or drug metabolism. Variants affecting pharmacokinetics are described in M. A. Rudek et al., The Handbook of Anticancer Pharmacokinetics and Pharmacodynamics, published by Springer Science & Business Media, 2014, which is hereby incorporated by reference in its entirety.

The subject genetic profile can include assaying for variants that impact cancer progression. Such mutations can be, for example, heritable mutations that reduce the efficiency of tumor suppressor gene products, such as TP53 or BRCA1.

In some embodiments, the subject profile includes non-genetic information. Such information can include the age of the subject, efficacy of other drugs the patient has received, clinical information regarding the subject, and family medical history. Clinical information regarding the subject can comprise additional clinical information, for example, organ function, such as liver and kidney function; blood cell count; heart function; lung and respiratory function; and infection status. Clinical information regarding the subject can comprise age, sex, gender, genetic profile, enzyme levels, organ function, quality of life, frequency of medical interventions, remission status, and/or patient outcome. The profile of the subject can include information about prior treatments. Treatments can be, for example, surgical removal, radiation, or chemotherapy administration. Information can be qualitative (indicating what treatment received), or quantitative, for example comprising dose, duration, and timing information. Subject information can include whether the subject is alive or deceased. Subject information can be collected at various time points to generate, for a population of subjects, a median survival rate, a 6-month survival rate, a 1-year survival rate, a 2-year survival rate, a 3-year survival rate, 5-year survival rate, or longer.

Determining a state (e.g., an initial state) can comprise obtaining information about the subject and assigning the subject to a state based on the information. In some cases, the states are determined based on a subset of the information. For example, states can be determined by clustering subjects from a training set, and a new subject can be assigned to a state by determining which cluster they are closest to.

Clustering can be used to convert quantitative data into categorical data. For example, certain cancer medications can cause liver damage. The level of liver enzymes (e.g., AST and ALT) in the blood of the subjects on such a cancer medication can be measured. Clustering or visual inspection of liver enzyme levels can reveal some subjects with elevated and some subjects with normal liver enzyme levels. The liver enzyme levels can be converted to categorical variables by defining subjects with liver enzymes above a given level as "elevated" and those below a given level as "normal."

Categorical data and quantitative data can be combined. In one exemplary method, categorical data can be converted for use in methods that require quantitative data by converting the categorical data to a 'dummy value.' For example, a patient with elevated liver enzyme levels can be assigned a value of 1, while a patient with normal liver enzyme levels can be assigned a value of 0. Other methods of converting categorical variables to quantitative variables include effects coding, contrast coding, and nonsense coding.

States can represent outcomes of interest (e.g., survival, remission status, or length of time prior to resistance emerging), which can be recorded. A set of subjects (e.g., a training set) can be used to determine the effect size and interactions of initial states and/or treatments on outcomes of interest determined. These effect sizes and interactions can be used to develop a classifier or predictive model. Methods to determine the effect size and interaction terms of features from initial states can include, for example, regression analysis, including linear and logarithmic regression analysis; nearest shrunken centroid analysis; stabilized linear discriminant analysis; Support Vector Machine; Gaussian Process; Conditional Inference Tree Forest; Random Forest; Nearest Centroid; Naive Bayes; Projection Pursuit LDA Tree; Multinomial Logistic Regression; Stump Decision Trees; Artificial Neural Networks; Binary Decision Trees; and/or Conditional Inference Trees. The accuracy and sensitivity of a classifier or predictive model can be determined by measuring prediction accuracy on a subset of subjects that were not used to construct the classifier or predictive model (e.g., a test set).

In some cases, the effect size of predictors is determined and low-impact variables are removed. Methods of variable selection are known in the art, and can include, for example, filter methods and/or wrapper methods for variable selection. Filter methods are based on general features, such as correlation of a variable with an outcome. Wrapper methods evaluate subsets of variables together to determine optimal combinations of variables. The selected variables can be used to determine the subset of information that is used to determine the state of a subject.

In some cases, the training set of subjects have tumors in the same tissue types. In some cases, the subjects are of a similar demographic profile, such as the same gender, the same age, the same ethnic background, or the same risk factors. Gender can be male or female. Exemplary risk factors include alcohol consumption, tobacco use and method of use, diet, exercise, occupation exposure to carcinogens, frequency of travel, and exposure to ultraviolet light and/or tanning. In some cases, the training set subjects are all patients with cancer. In some cases, the training set subjects are all patients with symptoms consistent with cancer who are being tested for cancer. In some cases, the training set subjects are patients with symptoms consistent with cancer who are being treated for cancer. Characteristics of the subjects can be included in the information about the each subject of the plurality of subjects.

The initial state of the subject can be used to determine the probability of a given subsequent state of the subject. The probability can be determined using a classifier or predictive model.

The classifier or predictive model can be used to identify a preferred treatment for a subject with a given profile. For example, using the classifier or predictive model to determine the probability of a given outcome for the subject can comprise generating one or more decision trees. A state at a first time point can be represented by a root node (which is an initial decision node), alternative treatments can be represented by decision branches. In some cases, decision branches can lead to terminal states (from which no further decision is taken) or intermediate state nodes, which, themselves, can be decision nodes. Intermediate state nodes can represent the emergence of genetic variants within one or more tumors of the subject that confer resistance of a tumor to a treatment; a result of a subsequent biopsy or imaging procedure; and/or generally a change or lack of change of the information from the subject at a time point. For example, an intermediate node can comprise information from the subject at 1 week after treatment, 2 weeks after treatment, 3 weeks after treatment, 4 weeks after treatment, 1 month after treatment, 2 months after treatment, 3 months after treatment, 6 months after treatment, 1 year after treatment, 2 years after treatment, 3 years after treatment, 4 years after treatment, or 5 years after treatment. Intermediate nodes can represent intermediate states where medical care providers make decisions regarding future treatment options (e.g., after a chemotherapy regimen has been completed, after a surgical intervention to remove a tumor, and at particular time points during an active monitoring regime).

Intermediate nodes can comprise information about the emergence of resistance to treatment. For example, the presence of particular variants in a tumor can indicate that resistance is emerging. The increase of a particular variant over time during treatment can indicate that the variant, or at least a second unseen variant, is associated with the emergence of resistance to the treatment. The probability that such a variant appears may be altered by the presence of particular variants that predispose the tumor down a particular evolutionary track. Intermediate nodes can comprise information about a subject's (e.g., patient's) health.

A tumor profile and/or subject profile can be determined at one or more subsequent time points. The information from the tumor and/or subject profile of subsequent time points can be used to determine subsequent states. Upon a determination of a subsequent state, the subsequent state can be used as a new initial state to update the probabilities of other subsequent nodes. For example, if the subject develops a KRAS variant that does not co-occur with a KRAS gene amplification event, the decision tree can be updated to reflect the reduced probability of a KRAS gene amplification event.

In some cases, subsequent states are represented by terminal nodes (e.g., the subject has died or has underwent complete remission). Subsequent states can be time points after treatments. Subsequent states can be points at which additional biopsies are taken. The biopsies can be liquid biopsies.

In some cases, terminal nodes represent a state at which no further medical decisions are taken. In some cases, terminal nodes represent the death of the subject. In some cases, terminal nodes represent inability to detect cancer in the subject.

In some cases, recommending a treatment comprises determining to which clusters generated for the classifier or predictive model the information from the subject belongs. Determining can be based on cluster boundaries determined by the methods described above. In some cases, determining can be based on selecting the cluster to which the information from the subject is closest. Selecting can be based at least in part on distance correlation.

Such a classifier or predictive model can be used to select treatments for a patient. For example, a patient with a given genetic profile and tumor genetic profile can be selected for a therapy that maximizes survival rates (e.g., five-year survival and/or remission rates). The patient can be monitored over time. If a genetic mutation arises that confers resistance to the therapy or provides an increased risk of developing resistance to the therapy, a second or different treatment can be administered that maximizes for five-year survival and/or remission based on the new state. The appropriate treatment can be selected to maximize for the subject's viability and/or number of years of survival.

Treatments are known to those of skill in the art, and examples are described in the NCCN Clinical Practice Guidelines in Oncology™ or the American Society of Clinical Oncology (ASCO) clinical practice guidelines. Examples of drugs used for treatments can be found in CMS approved compendia, including the National Comprehensive Cancer Network (NCCN) Drugs and Biologics Compendium™, Thomson Micromedex DrugDex®, Elsevier Gold Standard's Clinical Pharmacology compendium, and American Hospital Formulary Service—Drug Information Compendium®.

Computer Systems

Figure 7:
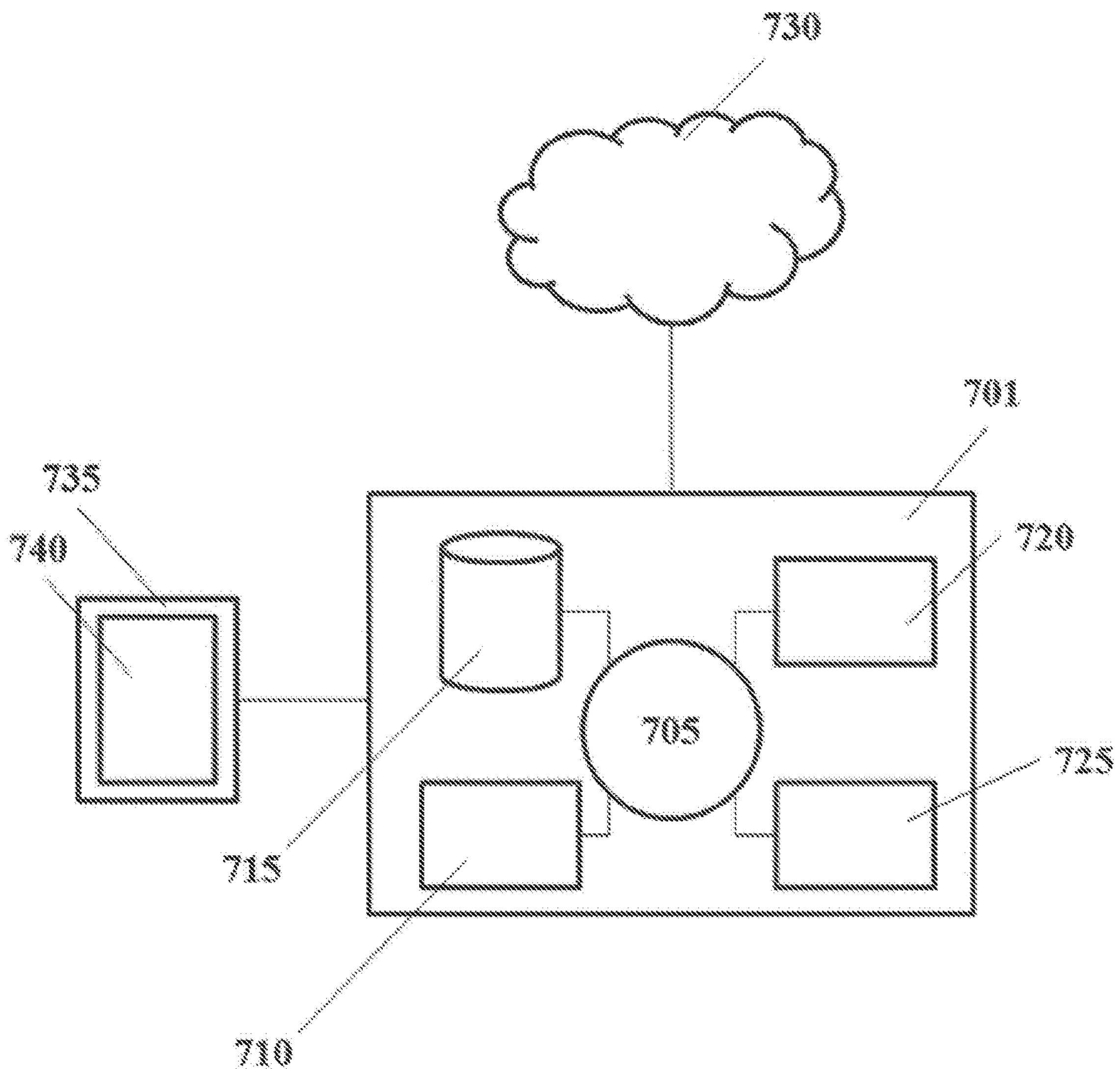
FIG. 7 shows a computer system that is programmed or otherwise configured to implement methods provided herein.

The present disclosure provides computer systems that are programmed to implement methods of the present disclosure. FIG. 7 shows a computer system 701 that is programmed or otherwise configured to detect or monitor cancer evolution.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., patient or healthcare provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, one or more results associated with or indicative of the evolution of cancer. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, implement methods of the present disclosure to detect or monitor cancer evolution.

EXAMPLES

Example 1: Constructing a Model of the Emergence of Treatment Resistance

Subjects with cancer undergo a physical screening to determine a patient profile, including their age, gender, type of cancer, stage of cancer, and organ function. The subjects undergo a blood draw, which is processed to remove cells to provide cell-free bodily fluid with nucleic acids. The nucleic acids are sequenced, and a patient genetic profile and tumor genetic profile is determined. The subjects are prescribed treatments by their physicians. The patients are followed over time, and a tumor genetic profile is obtained every three months. Patient outcomes are recorded at each time point.

A Hidden Markov model is constructed based on the probability that a patient with a given patient profile (including a patient genetic profile) and tumor genetic profile will have a particular patient outcome at any given time point.

Example 2: Using a Model of the Emergence of Treatment Resistance

A subject with cancer is admitted to a hospital. A subject profile and tumor profile are obtained. The subject profile and tumor profile are used as initial states for a model, such as the model generated in Example 1. The subject's outcomes are predicted based on the model, and treatments are chosen to maximize the subject's expected survival time (e.g., measured in months or years). The subject's tumor profile is updated every three months, and used as a new initial state input into the model. At a given subsequent time point, the tumor profile indicates that a subclone with resistance to the current treatment has emerged. In response, a new treatment is chosen to maximize the subject's expected survival time. The subject is given a second treatment (e.g., a second-line therapy) targeting tumor cells resistant to the first treatment (e.g., a first-line therapy).

Example 3: Representation of a Subject with a Decision Tree

A subject is associated with an initial node indicating that he is a 65-year-old male with colon cancer, and the tumor profile indicates that a low-frequency KRAS mutation is detected in the cell-free DNA of the subject. One branch emerging from the initial node indicates panitumumab and cetuximab treatment and a second branch indicates panitumumab and cetuximab treatment administered in conjunction with a mitogen-activated protein kinase enzyme (MEK) inhibitor. These branches connect to intermediate nodes that indicate resistance emergence and lack of resistance emergence. The probability of resistance emergence is lower for the intermediate nodes along the branch comprising co-treatment with a MEK inhibitor than the branch lacking co-treatment with a MEK inhibitor. Each intermediate node is associated with terminal nodes indicating death and complete remission. The probability of complete remission is higher for the terminal node along the decision branch that includes co-treatment with a MEK inhibitor.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the present disclosure. Other embodiments may be utilized and derived from the present disclosure, such that structural and logical substitutions and changes may be made without departing from the scope of the present disclosure. Accordingly, the present disclosure and the figures are to be regarded as illustrative rather than restrictive.

One or more embodiments of the present disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. The present disclosure is intended to cover any and all subsequent adaptations or variations of various embodiments. Combinations of the above embodiments, and other embodiments not specifically described herein, will be apparent to those of skill in the art upon reviewing the description.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A computer-implemented method, comprising:

receiving a plurality of sequencing reads, each sequencing read comprising a sequence tag that uniquely identifies a parent cell-free DNA (cfDNA) fragment;

grouping the sequencing reads into read families according to identical sequence tags and, for each read family, generating an error-corrected consensus sequence by aligning the reads of the read family and resolving per-base discrepancies that fail to satisfy a quality threshold;

for each of a plurality of subjects, constructing a molecular state vector that comprises, for each of a plurality of genomic loci, a quantitative allele-fraction value derived from the error-corrected consensus sequences;

storing, in a training datastore, a plurality of ordered pairs each including (i) a first molecular state vector captured at a first time point and (ii) a subsequent molecular state vector captured at a second time point later than the first time point; and training, with the plurality of ordered pairs, a predictive model that parameterizes state-transition probabilities between molecular state vectors conditioned on elapsed time, wherein the predictive model is configured to receive a query molecular state vector associated with an evaluation subject and compute, for each candidate subsequent molecular state vector, a probability that the evaluation subject will transition from the query molecular state vector to the candidate subsequent molecular state vector within a user-specified time window.

2. The computer-implemented method of claim 1, further comprising:

receiving a query molecular state vector associated with an evaluation subject; and applying the predictive model to the query molecular state vector to compute, for each candidate subsequent molecular state, a probability that the evaluation subject will transition from the query molecular state vector to the candidate subsequent molecular state within a user-specified time window.

3. The computer-implemented method of claim 2, further comprising automatically generating a treatment-recommendation message when the probability that the evaluation subject will transition from the query molecular state vector to the candidate subsequent molecular state exceeds a threshold.

4. The computer-implemented method of claim 2, wherein the second time point of the subsequent molecular state vector corresponds to the user-specified time window.

5. The computer-implemented method of claim 2, wherein, upon receipt of the query molecular-state vector, the predictive model retrieves a corresponding row of the state-transition-probability matrix and multiplies the corresponding row by the emission-probability matrix to generate, without re-processing the training datastore, a probability distribution over candidate observable molecular states at a future time point.

6. The computer-implemented method of claim 2, further comprising:

after elapse of the user-specified time window, acquiring a follow-up molecular-state vector for the evaluation subject;

appending, to the training datastore, an ordered pair that includes the query molecular-state vector and the follow-up molecular-state vector; and incrementally updating the parameters of the predictive model using the appended ordered pair.

7. The computer-implemented method of claim 1, wherein the plurality of genomic loci comprises at least fifty loci.

8. The computer-implemented method of claim 1, wherein the first molecular state vector comprises one or more somatic mutations.

9. The computer-implemented method of claim 1, wherein the subsequent molecular state vector comprises a viability state of a subject of the plurality of subjects indicative of the subject's survival rate.

10. The computer-implemented method of claim 1, wherein the sequence tag comprises a barcode.

11. The computer-implemented method of claim 1, wherein resolving per-base discrepancies that fail to satisfy the quality threshold further comprises:

assigning a quality score to each sequencing read of the plurality of sequencing reads; and removing sequencing reads with quality scores that fail to satisfy the quality threshold.

12. The computer-implemented method of claim 11, wherein the quality score of a sequencing read is based on a length of the sequencing read.

13. The computer-implemented method of claim 1, wherein the training datastore comprises, for at least one of the plurality of subjects, molecular state vectors captured at at least three time points.

14. The computer-implemented method of claim 1, wherein training the predictive model comprises fitting a discrete time hidden-Markov model (HMM).

15. The computer-implemented method of claim 1, further comprising:

assigning a mapping score to each sequencing read of the plurality of sequencing reads; and removing sequencing reads with mapping scores that fail to satisfy a mapping threshold.

16. The computer-implemented method of claim 15, wherein the mapping score of a sequencing read is indicative of a likelihood of being mapped incorrectly.

17. The computer-implemented method of claim 1, further comprising:

generating an electronic report comprising the probability computed by the predictive model.

18. The computer-implemented method of claim 1, wherein storing the plurality of ordered pairs in the training datastore comprises storing the plurality of ordered pairs in a matrix.

19. The computer-implemented method of claim 1, wherein the probability that the evaluation subject will transition from the query molecular state vector to the candidate subsequent molecular state vector is computed based on the query molecular state vector.

20. The computer-implemented method of claim 1, further comprising, for each subject, determining whether a proportion of one or more somatic mutations is increasing or decreasing between the first time point and the second time point.

* * * * *